(12) United States Patent
Mori et al.

(10) Patent No.: US 11,045,663 B2
(45) Date of Patent: Jun. 29, 2021

(54) X-RAY FLUOROSCOPY DEVICE AND X-RAY FLUOROSCOPY METHOD

(71) Applicant: Shimadzu Corporation, Kyoto (JP)

(72) Inventors: Shinichiro Mori, Chiba (JP); Wataru Takahashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/347,048

(22) PCT Filed: Jul. 20, 2017

(86) PCT No.: PCT/JP2017/026330
§ 371 (c)(1),
(2) Date: May 2, 2019

(87) PCT Pub. No.: WO2018/083844
PCT Pub. Date: May 11, 2018

(65) Prior Publication Data
US 2020/0069967 A1 Mar. 5, 2020

(30) Foreign Application Priority Data
Nov. 2, 2016 (JP) .............................. JP2016-215438

(51) Int. Cl.
*G06K 9/00* (2006.01)
*A61N 5/10* (2006.01)
(Continued)

(52) U.S. Cl.
CPC .............. *A61N 5/10* (2013.01); *A61B 6/4225* (2013.01); *A61B 6/4429* (2013.01); *A61N 5/01* (2013.01);
(Continued)

(58) Field of Classification Search
CPC ................................................... G06T 7/0012
See application file for complete search history.

(56) References Cited

U.S. PATENT DOCUMENTS

| 6,307,914 B1 | 10/2001 | Kunieda et al. |
| 2005/0069208 A1 | 3/2005 | Morisada |
| (Continued) | | |

FOREIGN PATENT DOCUMENTS

| JP | 3053389 B1 | 4/2000 |
| JP | 2004030629 A | 1/2004 |
| (Continued) | | |

OTHER PUBLICATIONS

Written Opinion of the ISA for PCT application PCT/JP2017/026330 dated Oct. 17, 2017.
(Continued)

*Primary Examiner* — Oneal R Mistry
(74) *Attorney, Agent, or Firm* — Muir Patent Law, PLLC

(57) ABSTRACT

A control unit 30 includes: an image storage unit 31 constituted by a first image storage unit 32 that stores multiple templates created on the basis of an image including a specific site of a subject and a second image storage unit 33 that stores multiple positive images created on the basis of an image including the specific site of the subject; a learning unit 34 that, on the basis of the multiple positive images, creates a discriminator by machine learning; a position selection unit 35 that, with use of multiple images obtained by collecting an image including the specific site of the subject at a predetermined frame rate, selects a region including the specific site by machine learning using the discriminator; and a position detection unit 36 that detects the position of the specific site by performing template matching using the multiple templates on the region including the specific site selected by the position selection unit 35.

12 Claims, 19 Drawing Sheets

(51) Int. Cl.
  *A61B 6/00*  (2006.01)
  *A61N 5/01*  (2006.01)
  *G06T 7/00*  (2017.01)

(52) U.S. Cl.
  CPC .. *G06T 7/0012* (2013.01); *G06T 2207/10116* (2013.01)

(56) References Cited

U.S. PATENT DOCUMENTS

| | | | |
|---|---|---|---|
| 2010/0246915 A1* | 9/2010 | Yamakoshi | A61B 6/032 |
| | | | 382/131 |
| 2015/0087881 A1* | 3/2015 | Miyamoto | A61B 6/5211 |
| | | | 600/1 |
| 2016/0109544 A1 | 4/2016 | Kuhara et al. | |
| 2016/0136458 A1 | 5/2016 | Taguchi et al. | |
| 2016/0175614 A1 | 6/2016 | Taguchi et al. | |
| 2017/0193160 A1* | 7/2017 | Long | A61B 34/25 |
| 2017/0197098 A1 | 7/2017 | Hirasawa et al. | |
| 2019/0320995 A1* | 10/2019 | Amiri | A61B 6/463 |

FOREIGN PATENT DOCUMENTS

| | | |
|---|---|---|
| JP | 2005078376 A | 3/2005 |
| JP | 2010-187991 A | 2/2010 |
| JP | 2013246184 A | 12/2013 |
| JP | 2015131023 A | 7/2015 |
| JP | 2016-96902 A | 5/2016 |
| JP | 2016-116659 A | 6/2016 |
| WO | 2016046870 A1 | 3/2016 |

OTHER PUBLICATIONS

International Search Report for PCT application PCT/JP2017/026330 dated Oct. 17, 2017.
Japanese Office Action dated Mar. 9, 2021, for corresponding Japanese Patent Application No. 2017-163056.

* cited by examiner

X-RAY FLUOROSCOPY DEVICE AND X-RAY FLUOROSCOPY METHOD

TECHNICAL FIELD

The present invention relates to an X-ray fluoroscopy device and X-ray fluoroscopy method that makes an X-ray detector detect X-rays radiated from an X-ray tube and passing through a subject to acquire images including a specific site of the subject, and detects the positions of the specific site from the images including the specific site of the subject to track the movement of the specific site.

BACKGROUND ART

In radiotherapy that radiates a radiation beam such as X-rays or a proton beam as a treatment beam to an affected area such as a tumor, the radiation beam has to be accurately radiated to the affected area. However, there may be not only a case in which a subject moves the body, but a case in which movement occurs in the affected area itself. For example, a tumor near the lungs greatly moves on the basis of breathing. For this reason, there has been proposed a radiotherapy apparatus having a configuration that places a metallic marker having a spherical shape near a tumor, and detects the position of the marker by an X-ray fluoroscopy device to control the radiation of a treatment radiation beam (see Patent Literature 1).

In such a radiotherapy apparatus, the marker placed in the body is imaged using a first X-ray fluoroscopic mechanism constituted by a first X-ray tube and a first X-ray detector and a second X-ray fluoroscopic mechanism constituted by a second X-ray tube and a second X-ray detector, and using a two-dimensional fluoroscopic image by the first X-ray fluoroscopic mechanism and a two-dimensional fluoroscopic image by the second X-ray fluoroscopic image, three-dimensional position information is obtained. In addition, by continuously performing X-ray fluoroscopy to calculate the three-dimensional position information on the marker in real time, the marker in a site exhibiting movement is detected with high accuracy. Then, by controlling the radiation of the treatment radiation beam on the basis of the position information on the detected marker, the radiation beam can be highly accurately radiated corresponding to the movement of the tumor. To obtain the position information on the marker, template matching using templates is performed.

Meanwhile, as described above, in order to detect the movement of a tumor using a marker, it is necessary to preliminarily place the marker in the body of a subject. On the other hand, in recent years, there has been proposed a method called markerless tracking that omits placing a marker by using a specific site such as a tumor region of a patient instead of a marker.

CITATION LIST

Patent Literature

[Patent Literature 1]
  Japanese Patent No. 3053389

SUMMARY OF INVENTION

Technical Problem

The X-ray fluoroscopy device is one capable of detecting even a marker or specific site having a shape other than a spherical shape, but in particular, when detecting a specific site, requested to further improve detection accuracy. Also, when evaluating the degree of similarity using a large number of templates, there occurs the problem of increasing calculation cost to make real-time processing difficult.

The present invention has been made in order to solve the above-described problems, and a first object thereof is to provide an X-ray fluoroscopy method and X-ray fluoroscopy device capable of further improving the detection accuracy of a specific site, and also even when performing template matching using images of a specific site of a subject, more easily performing calculation to detect the position of the specific site in real time.

Also, in markerless tracking using a specific site of a subject instead of a spherically-shaped marker, the recognizable shape of the specific site is different depending on a breathing phase of the subject, and therefore even if templates are created using an image obtained by imaging the specific site at a single breathing phase, only this does not enable accurate template matching to be performed. For this reason, in order to respond to the fact that the recognizable shape of the specific site is different depending on a breathing phase of the subject, multiple images including the specific sites imaged at different breathing phases just before radiotherapy have to be stored as templates, and also template matching has to be performed using the preliminarily stored multiple templates on images imaged at regular time intervals.

When using the multiple templates as described above, it is necessary for an operator to fluoroscope the subject with X-rays just before the radiotherapy, and specify the position of the tumor at each breathing phase to create a template while viewing an X-ray image. For this reason, it takes time to create the multiple templates, causing the problem of not only being painful for the patient but a reduction in throughput for therapy.

The present invention has been made in order to solve the above-described problem, and a second object thereof is to provide an X-ray fluoroscopy device and X-ray fluoroscopy method capable of eliminating the time required for creating templates just before radiotherapy to quickly perform moving body tracking, as well as more accurately detect the position of a specific site by performing machine learning using DRR images preliminarily created on the basis of CT image data prior to radiotherapy.

In addition, when detecting the position of a specific site by image recognition, and when the specific site is arranged near a bone region, the contrast of the bone region is larger than the contrast of the specific site, and therefore when performing machine learning, there occurs the problem of being unable to accurately detect the position of the specific site because the bone region is learned rather than the specific site.

The present invention has been made in order to solve the above-described problem, and a third object thereof is to provide an X-ray fluoroscopy device and X-ray fluoroscopy method capable of, even when a specific site is present near a bone region, accurately detecting the position of the specific site.

Further, in radiotherapy, it is preferable to radiate a treatment beam not only when the position of a specific site coincides with a predetermined position but only when a breathing phase of a subject coincides with a specific phase. That is, this is because a treatment plan for the subject is created on condition that a breathing phase of the subject coincides with the specific phase, and therefore even when the position of the specific site coincides with the predetermined position, when the breathing phase is different from that at the time of creating the treatment plan, an exposure dose as in the treatment plan is ineffective. Note that since the specific site is moved by peristaltic movement or the like other than breathing, even when the specific site is arranged at the predetermined position, there is no assurance that the breathing phase is the same.

The present invention has been made in order to solve the above-described problem, and a fourth object thereof is to provide an X-ray fluoroscopy device and X-ray fluoroscopy method capable of, when a specific site is at a predetermined position and a breathing phase of a subject coincides with a specific phase, radiating a treatment beam by specifying the position of the specific site and also the breathing phase of the subject.

Solution to Problem

A first invention is an X-ray fluoroscopy device configured to collect an image including a specific site of the subject captured therein and to detect a position of the specific site to track its movement, the X-ray fluoroscopy device comprising: an X-ray tube; an X-ray detector for detecting an X-ray radiated from the X-ray tube and having passed through a subject an image storage unit for storing a template configured for template matching, the template being created on a basis of an image including the specific site of the subject, and a positive image for machine learning, the positive image being created on a basis of an image including the specific site of the subject; a learning unit for, on a basis of the positive image stored in the image storage unit, creating a discriminator by the machine learning; and a position detection unit for detecting a position of the specific site by, on an image obtained by fluoroscoping a region including the specific site of the subject, performing both of the template matching using the template and discrimination using the discriminator.

A second invention is such that the position detection unit is operable to perform the template matching and the discrimination using the discriminator in this order or in the reverse order thereof, or is operable to simultaneously perform the template matching and the discrimination using the discriminator.

A third invention is an X-ray fluoroscopy device configured to collect an image including a specific site of the subject captured therein and to detect a position of the specific site to track its movement, the X-ray fluoroscopy device comprising: an X-ray tube; an X-ray detector for detecting an X-ray radiated from the X-ray tube and having passed through a subject an image storage unit for storing a template configured for template matching, the template being created on a basis of an image including the specific site of the subject, and a positive image for machine learning; a learning unit for, on a basis of the positive image stored in the image storage unit, creating a discriminator by the machine learning; a position selection unit for, with use of an image collected by the X-ray tube and the X-ray detector, selecting a specific site possible position by discrimination using the discriminator; and a position detection unit for detecting a position of the specific site by performing the template matching using the template stored in the image storage unit on a region including the specific site, the region being selected by the position selection unit.

A fourth invention is such that the machine learning is SVM, Boosting, or a neural network.

A fifth invention is such that the template and the positive image are respectively created on the basis of the same image including the specific site.

A sixth invention is an X-ray fluoroscopy method that, by making an X-ray detector detect an X-ray radiated from an X-ray tube and passing through a subject and collecting an image including a specific site of the subject, detects a position of the specific site to track movement of the specific site, and includes: a storage step of storing a template configured for template matching, which is created on the basis of an image including the specific site of the subject, and a positive image for machine learning, which is created on the basis of an image including the specific site of the subject; a learning step of, on the basis of the positive image stored in the storage step, creating a discriminator by the machine learning; a fluoroscopy step of making the X-ray detector detect the X-ray radiated from the X-ray tube and passing through the subject, and collecting an image including the specific site of the subject; and a position detection step of detecting a position of the specific site by, on an image obtained in the fluoroscopy step, performing both of the template matching using the template and performing discrimination using the discriminator.

A seventh invention is an X-ray fluoroscopy method that, by making an X-ray detector detect an X-ray radiated from an X-ray tube and passing through a subject and collecting an image including a specific site of the subject, detects a position of the specific site to track movement of the specific site, and includes: an storage step of storing a template configured for template matching, which is created on the basis of an image including the specific site of the subject, and a positive image for machine learning; a learning step of, on the basis of multiple positive images stored in the image storage step, creating a discriminator by the machine learning; a fluoroscopy step of making the X-ray detector detect the X-ray radiated from the X-ray tube and passing through the subject, and collecting an image including the specific site of the subject; a position selection step of, with use of an image obtained in the fluoroscopy step, selecting a possible position of the specific site by discrimination using the discriminator; and a position detection step of detecting a position of the specific site by performing the template matching using the template stored in the image storage step on the possible position of the specific site, which is selected in the position selection step.

An eighth invention is an X-ray fluoroscopy device that makes an X-ray detector detect an X-ray radiated from an X-ray tube and passing through a subject to acquire an image including a specific site of the subject, and detects a position of the specific site from an image including the specific site of the subject to track movement of the specific site, and includes: an DRR image creation unit that creates multiple DRR images including the specific site by, on CT image data created at the time of storing a treatment plan, performing virtual fluoroscopic projection simulating geometric fluoroscopic conditions of the X-ray tube and the X-ray detector with respect to the subject; a discriminator creation unit that, by performing machine learning on the DRR images created in the DRR image creation unit, creates a discriminator for recognizing the specific site; and a position detection unit for detecting a position of the specific site by performing discrimination using the discriminator created in the discriminator creation unit on an images including the specific site of the subject, which is obtained by making the X-ray detector detect the X-ray radiated from the X-ray tube and passing through the subject.

A ninth invention is such that the DRR image creation unit creates the DRR images by changing parameters including at least one of a projection coordinate and an angle in the geometric fluoroscopic conditions or performing image processing including at least one of rotation, deformation, and scaling of an image.

A tenth invention is such that the DRR image creation unit performs at least one of contrast change, noise addition, and edge enhancement on the created DRR images.

An eleventh invention is such that the DRR image creation unit creates the multiple DRR images including the specific site on the basis of four-dimensional CT image data consisting of a three-dimensional CT image data group that is created at the time of storing the treatment plan and on a region including the specific site at multiple continuous breathing phases.

A twelfth invention is such that the DRR image creation unit creates the multiple DRR images including the specific site on the basis of pieces of CT image data at multiple breathing phases including a breathing phase at which a treatment beam is radiated to the subject among the four-dimensional image data consisting of the three-dimensional CT image data group that is created at the time of storing the treatment plan and on the region including the specific site at the multiple continuous breathing phases.

A thirteenth invention is such that on the basis of the CT image data created at the time of storing the treatment plan, the DRR image creation unit creates a DRR image in which the specific site is included and from which a bone region of the subject is removed.

A fourteenth invention is such that on the basis of a CT value in the CT image data created at the time of storing the treatment plan, the DRR image creation unit creates CT image data from which the bone region of the subject is removed, and on the basis of the CT image data from which the bone region is removed, creates the DRR image in which the specific site is included and from which the bone region of the subject is removed.

A fifteenth invention is such that when creating a DRR image by performing a line integral of a voxel value in the CT image data created at the time of storing the treatment plan, on the basis of the voxel value, the DRR image creation unit creates the DRR image in which the specific site is included and from which the bone region of the subject is removed.

A sixteenth invention further includes an X-ray image creation unit that creates multiple X-ray images including the specific site by making the X-ray detector detect the X-ray radiated from the X-ray tube and passing through the subject and collecting an image including the specific site of the subject; and a correction unit that, with use of the X-ray images created by the X-ray image creation unit, corrects the discriminator created in the discriminator creation unit.

A seventeenth invention further includes an X-ray image creation unit that creates multiple X-ray images including the specific site by making the X-ray detector detect the X-ray radiated from the X-ray tube and passing through the subject and collecting an image including the specific site of the subject, in which the discriminator creation unit performs machine learning on the DRR images created in the DRR image creation unit and on the X-ray images created in the X-ray image creation unit, and thereby creates the discrimination for recognizing the specific site.

An eighteenth invention is such that the discriminator is a multi-class discriminator for recognizing the specific site at each breathing phase of the subject, and the position detection unit detects the position of the specific site and a breathing phase of the subject by performing multi-class discrimination using the multi-class discriminator created in the discriminator creation unit on an image including the specific site of the subject, which is obtained by making the X-ray detector detect the X-ray radiated from the X-ray tube and passing through the subject.

A nineteenth invention is an X-ray fluoroscopy method that makes an X-ray detector detect an X-ray radiated from an X-ray tube and passing through a subject to acquire an image including a specific site of the subject, and from an image including the specific site of the subject, detects a position of the specific site to track movement of the specific site, and includes: a DRR image creation step of creating multiple DRR images including the specific site on the basis of CT image data created at a time of storing a treatment plan; a discriminator creation step of, by performing machine learning on the DRR images created in the DRR image creation step, creating a discriminator for recognizing the specific site; a fluoroscopy step of making the X-ray detector detect the X-ray radiated from the X-ray tube and passing through the subject to obtain an image including the specific site of the subject; and a position detection step of detecting a position of the specific site by performing discrimination using the discriminator created in the discriminator creation step on an image obtained in the fluoroscopy step.

Advantageous Effects of Invention

According to the first to seventh inventions, the detection accuracy of the specific site can be improved by using the template matching and the machine learning in combination.

According to the third and seventh inventions, even when performing the template matching using the template created on the basis of an image including the specific site of the subject, calculation can be more easily performed to detect the position of the specific site in real time.

According to the fourth invention, the machine learning can be more quickly performed.

According to the fifth invention, multiple templates and positive images can be more efficiently created in the single step.

According to the eighth to nineteenth inventions, by performing the machine learning using the DRR images preliminarily created on the basis of the CT image data prior to radiotherapy, time having been required to create templates just before the radiotherapy in the past can be eliminated to quickly perform moving body tracking.

According to the ninth invention, since the parameters including the projection coordinate and the angle in the geometric fluoroscopy conditions are changed or the image processing including the rotation, deformation, and scaling of an image is performed, even when the specific site is non-reproducibly moved or deformed, the position of the specific site can be accurately detected. In addition, since a large number of DRR image can be created, a custom-made discriminator corresponding to each patient can be learned, and in addition, even when using DRR images of a low frame rate or even when a background is imaged on the specific site, the position of the specific site can be accurately detected.

According to the tenth invention, since the contrast change, noise addition, and edge enhancement are performed on the created DRR images, even when there occurs a difference in image quality between the DRR images and X-ray images, the position of the specific site can be accurately detected.

According to the eleventh and twelfth inventions, since the multiple DRR images including the specific site are created on the basis of the four-dimensional CT image data consisting of the three-dimensional image data group on the region including the specific site at the multiple continuous breathing phases, the machine learning can be performed with a site not moving together with the specific site of the subject being removed, and therefore accurate moving body tracking can be performed.

According to the thirteenth to fifteenth inventions, since DRR image from which the bone region of the subject is removed is created, the machine learning can be performed with the bone region of the subject removed, and therefore accurate moving body tracking can be performed.

According to the sixteenth invention, since the discriminator created in the discriminator creation unit is corrected using the X-ray images, the discriminator can be quickly corrected without using a large number of X-ray images, and also the position of the specific site can be more accurately detected.

According to the seventeenth invention, by performing the machine learning on the DRR images created on the basis of the CT image data and on the X-ray images created by X-ray imaging, the discriminator can be quickly created without using a large number of X-ray images, and also the position of the specific site can be more accurately detected.

According to the eighteenth invention, together with the position of the specific site, a breathing phase of the subject at the time can also be specified. For this reason, when the specific site is at a predetermined position and a breathing phase of the subject coincides with a specific phase, a treatment beam can be radiated.

DESCRIPTION OF EMBODIMENTS

Figure 1:
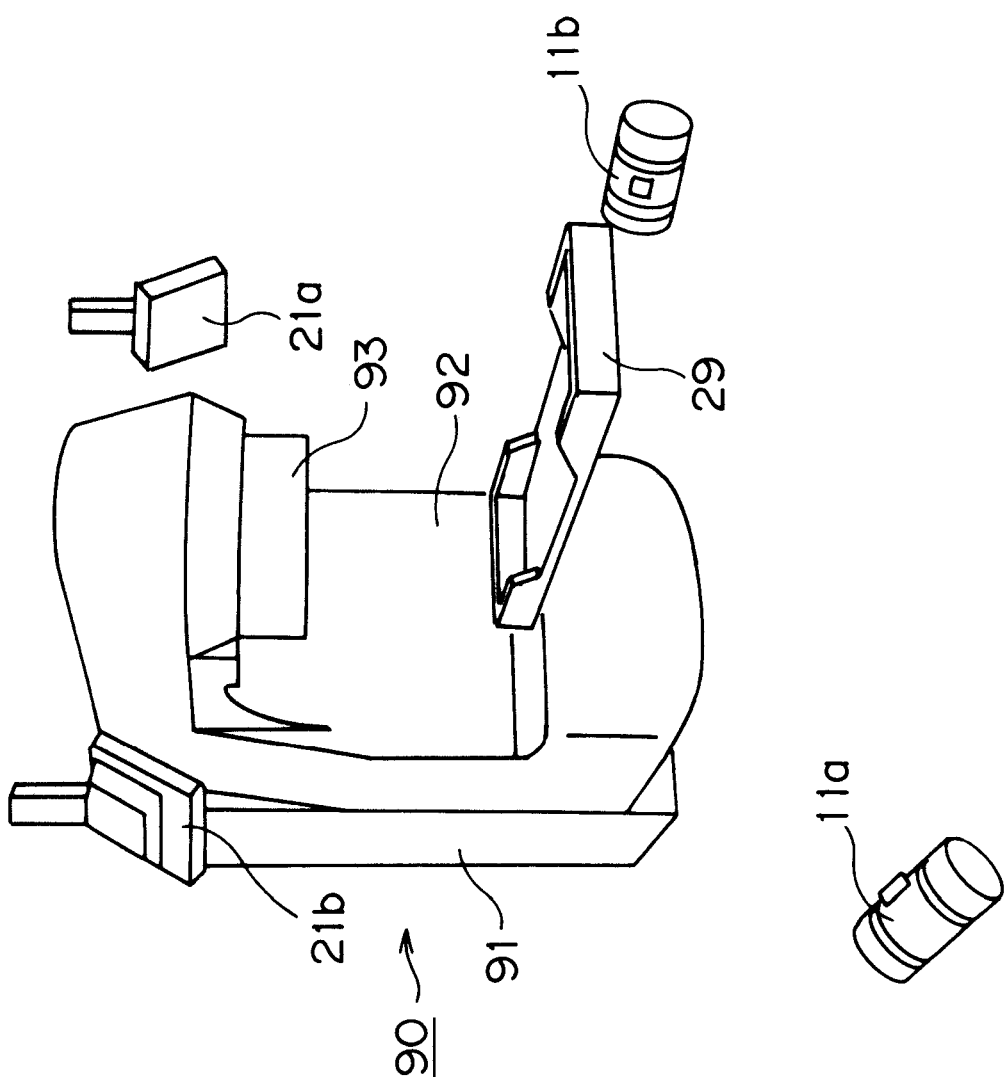
FIG. 1 is a perspective view illustrating the X-ray fluoroscopy device according to the present invention together with a radiation irradiator 90.

In the following, embodiments of the present invention will be described. FIG. 1 is a perspective view illustrating the X-ray fluoroscopy device according to the present invention together with a radiation irradiator 90. The X-ray fluoroscopy device and the radiation irradiator 90 constitute a radiotherapy apparatus.

The radiation irradiator 90 is one that radiates a radiation beam to a subject on an examination table 29 called a couch, and includes: a gantry 92 installed swingably with respect to a base 91 installed on a floor surface of a treatment room; and a head 93 that is disposed on the gantry 92 and emits a treatment beam. According to the radiation irradiator 90, the gantry 92 swings with respect to the base 91, and thereby the radiation direction of the treatment beam radiated from the head 93 can be changed. For this reason, the treatment beam can be radiated to an affected area such as a tumor in the subject from various directions.

The X-ray fluoroscopy device used together with the radiation irradiator 90 is one that performs X-ray fluoroscopy for performing moving body tracking that specifies the position of the affected area of the subject. That is, at the time of radiotherapy using the above-described radiation irradiator 90, it is necessary to accurately radiate the radiation beam to the affected area that moves along with the body movement of the subject. This requires a configuration that performs so-called the moving body tracking that, by preliminarily registering a site having a specific shape in the subject, such as a tumor, as a specific site, and continuously fluoroscoping the specific site with X-rays to calculate three-dimensional position information on the specific site, detects the specific site with high accuracy. As described, a moving body tracking method that, instead of placing a marker near an affected area in a subject as conventional, uses an image of a specific site such as a tumor in a subject as a marker is referred to as markerless tracking.

The X-ray fluoroscope device includes a first X-ray tube 11a, a second X-ray tube 11b, a first flat panel detector 21a, and a second flat panel detector 21b. X-rays radiated from the first X-ray tube 11a transmit through the subject on the examination table 29, and are then detected by the first flat panel detector 21a. The first X-ray tube 11a and the first flat panel detector 21a constitute a first X-ray imaging system. X-rays radiated from the second X-ray tube 11b transmit through the subject on the examination table 29, and are then detected by a second flat panel detector 21b. The second X-ray tube 11b and the second flat panel detector 21b constitute a second X-ray imaging system.

Figure 2:
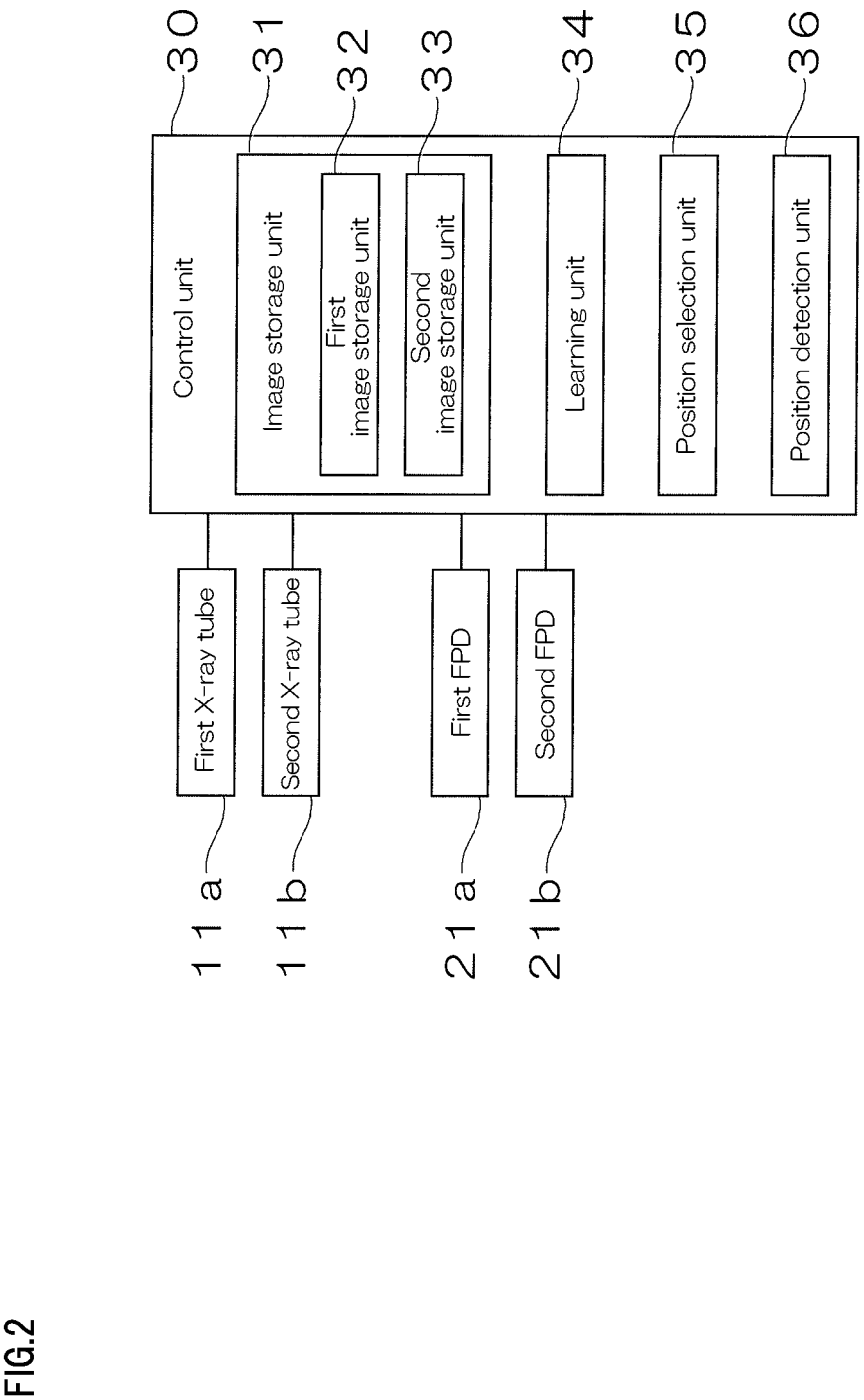
FIG. 2 is a block diagram illustrating a main control system of the X-ray fluoroscopy device according to the present invention.

FIG. 2 is a block diagram illustrating a main control system of the X-ray fluoroscopy device according to the present invention.

The X-ray fluoroscopy device is provided with a control unit 30 that includes: a CPU as a processor that performs logic operations; a ROM in which an operation program required to control the device is stored; a RAM in which data and the like are temporarily stored at the time of control, and the like, and controls the whole of the device. The control unit 30 is connected to the above-described first X-ray tube 11a, second X-ray tube 11b, first flat panel detector 21a, and second flat panel detector 21b.

The control unit 30 includes an image storage unit 31 constituted by: a first image storage unit 32 adapted to store one or more templates that are created on the basis of images including the specific site of the subject and for template matching; and a second image storage unit 33 adapted to store one or more positive images that are created on the basis of images including the specific sites of the subject and for machine learning. Also, the control unit 30 includes: a learning unit 34 that creates a discriminator (described below) by the machine learning on the basis of the positive images stored in the second image storage unit 33; a position selection unit 35 that, with use of multiple images obtained by collecting images including the specific site of the subject at a predetermined frame rate, selects one or more possible positions of the specific site by the machine learning using the discriminator; and a position detection unit 36 that detects the position of the specific site by performing the template matching using the multiple templates stored in the first image storage unit 32 on one or more possible positions selected by the position selection unit 35.

Figure 3:
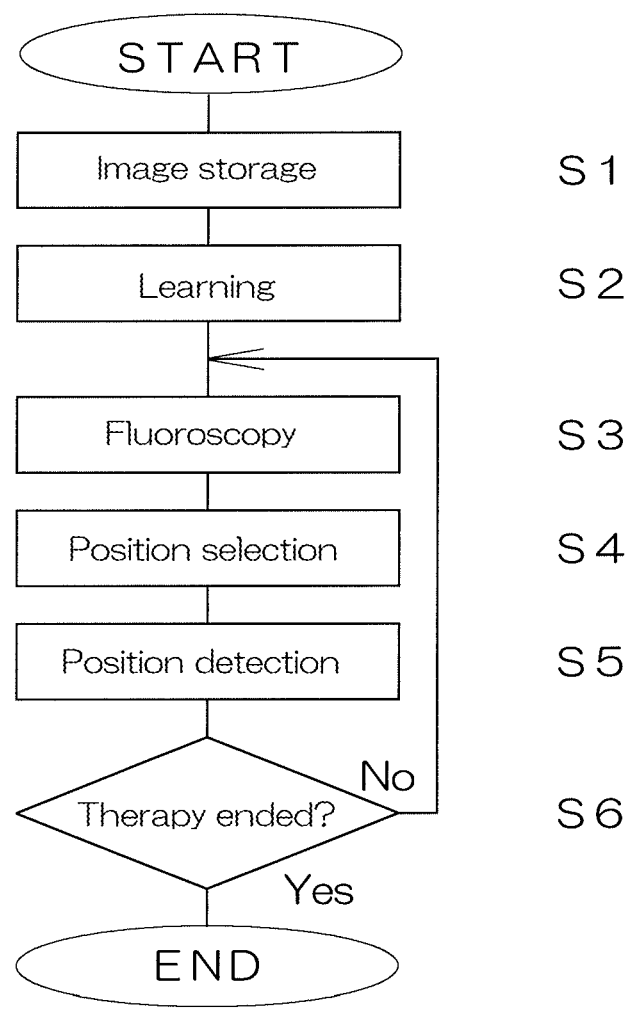
FIG. 3 is a flowchart illustrating a moving body tracking operation using the X-ray fluoroscopy device according to the present invention.

Next, an operation of performing the moving body tracking that detects positions of the specific site moving along with the body movement of the subject by using the X-ray fluoroscopy device having the above-described configuration will be described. FIG. 3 is a flowchart illustrating the moving body tracking operation using the X-ray fluoroscopy device according to the present invention. The following operation is performed on the two X-ray imaging systems in the same manner.

When performing the moving body tracking using the X-ray fluoroscopy device according to the present invention, an image storage step is first performed (Step S1). In this image storage step, images including the specific site of the subject placed on the examination table 29 are imaged using the above-described first X-ray imaging system and second X-ray imaging system. Then, on the basis of the X-ray images obtained by this imaging, one or more templates for template matching, and one or more positive images for machine learning are created. The created multiple templates for template matching are stored in the first image storage unit 32 in the image storage unit 31 illustrated in FIG. 2. Also, the multiple positive images for machine learning are stored in the second image storage unit 33 in the image storage unit 31 illustrated in FIG. 2. Further, in the second image storage unit 33 in the image storage unit 31, negative images used for the machine learning are also stored.

Figure 4:
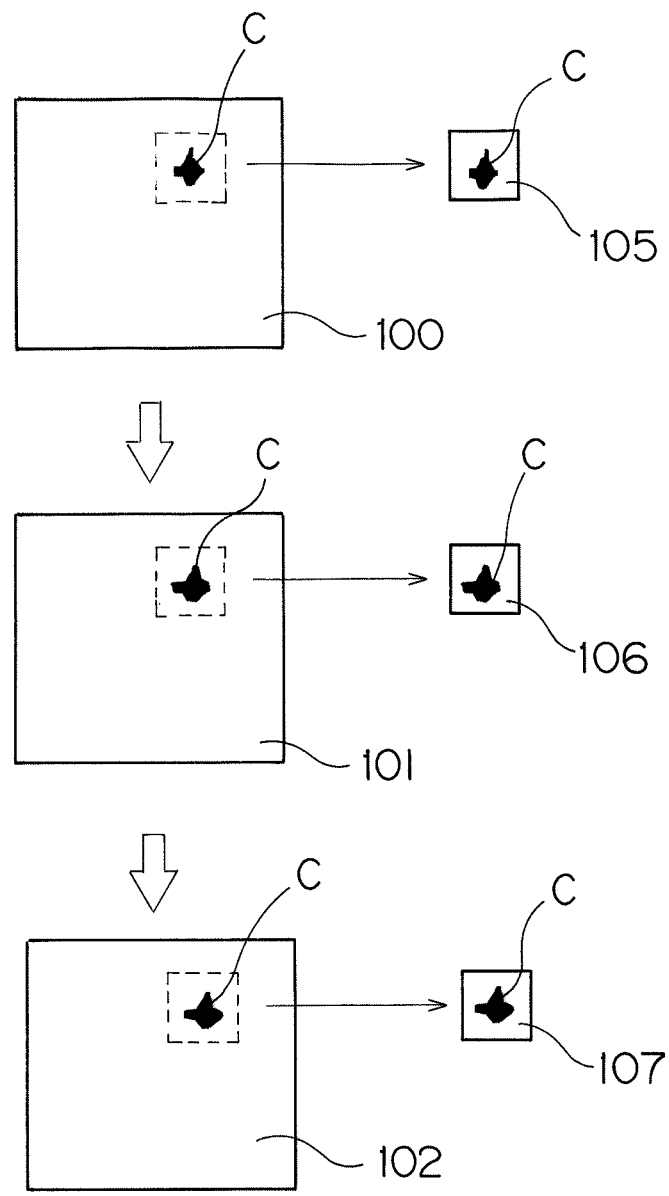
FIG. 4 is an explanatory diagram illustrating a step of creating templates and positive images.

FIG. 4 is an explanatory diagram illustrating a step of creating templates and positive images.

Note that this diagram illustrates a state where three images 100, 101, 102 including the specific site C of the subject, such as a tumor, are continuously imaged. In practice, more images of this kind are imaged at the predetermined frame rate. An operator trims a unit corresponding to the specific site C from these images 100, 101, 102. Instead of performing the trimming by the operator as described, the projection position of the specific site C at each phase may be acquired from positions of the specific site in 4DCT (four-dimensional CT image data consisting of a three-dimensional CT image data group imaged with time) used in a treatment plan, and from the correspondence relationships between the images 100, 101, 102 and the 4DCT, positions of the specific site C may be recognized to automatically perform the trimming. Alternatively, an approximate position of the specific site C may be acquired using the 4DCT and the operator may correct it.

Each of trimmed images 105, 106, 107 illustrated in FIG. 4 serves as a template used for multi-template matching, and registered in the first image storage unit 32. Also, the trimmed images 105, 106, 107 illustrated in FIG. 4, and/or images obtained by automatically slightly translating, rotating (e.g., approximately 10 degrees), deforming, and scaling the trimmed images 105, 106, 107 are created as positive images for machine learning, and registered in the second image storage unit 33. The reason that the images obtained by translating, rotating, deforming, and scaling the trimmed images 105, 106, 108 are also used as the positive images is to make it possible to surely track the specific site C even when the specific site C of the subject, such as a tumor, is moved or deformed in the body of the subject. Further, arbitrary regions among regions other than the trimmed images 105, 106, 107 in the images 100 are automatically extracted, created as negative images, and registered in the second image storage unit 33. In addition, instead of creating the negative images every time, preliminarily stored negative images may be used.

As described above, as each of sets of the multiple templates and the multiple positive images, images created on the basis of the same image are used. That is, as each template and each positive image, ones trimmed from the same image including the specific site C are used. This makes it possible to efficiently create the multiple templates and the multiple positive images in the single step.

Next, a learning step in the machine learning is performed (Step S2). In this learning step, by performing the learning using the multiple positive images stored in the second image storage unit 33, one discriminator for the machine learning is created. The discriminator consists of a calculation expression and parameters, and is an index used to track the position of the specific site C using the machine learning. The discriminator is created by the machine learning using the multiple positive images and the multiple negative images stored in the second image storage unit 33. The calculation expression is determined by the type (described below) of the machine learning; however, the calculation expression itself is a well-known technique, and therefore description is omitted here. The learning step requires a certain period of time. However, by performing the learning step during a period after imaging of the images including the specific site C in the subject has been completed in advance until the radiotherapy is actually performed, placing a burden on the subject is not required. In addition, the imaging of the images including the specific site C may be performed just before the below-described radiotherapy or may be performed in advance prior to it.

In addition, as the above-described type of the machine learning, for example, SVM (Support Vector Machine) can be used. The SVM is one of learning models most superior in quickness and high in recognizing performance among many methods when performing pattern recognition. Also, as the machine learning superior in quickness, instead of the SVM, Boosting based on a Haar-like feature value or the like, or a neural network such as Deep Learning may be used.

Upon completion of the above preparation steps, the subject is again placed on the examination table 29, the moving body tracking through X-ray fluoroscopy is performed by the X-ray fluoroscopy device according to the present invention, and a radiation beam is radiated from the radiation irradiator 90 to start the radiotherapy.

When starting the radiotherapy, the X-ray fluoroscopy is first performed (Step S3). The X-ray fluoroscopy is performed at the predetermined frame rate, for example, at approximately 30 fps (frame per second). Then, using multiple X-ray images acquired at the predetermined frame rate, one or more possible positions of the specific site C are selected by discrimination using the discriminator preliminarily created by the machine learning (Step S4).

Figure 5:
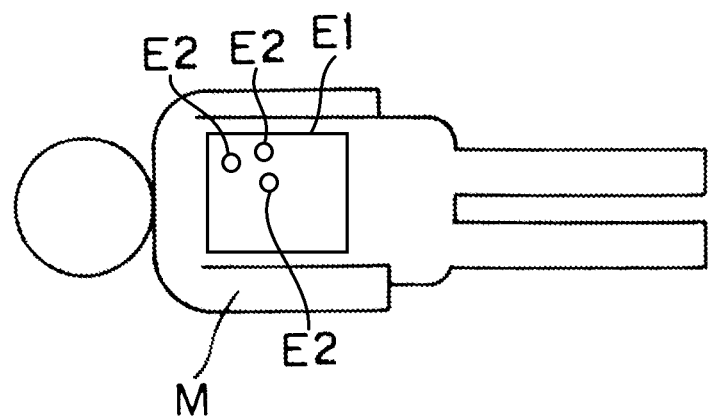
FIG. 5 is an explanatory diagram schematically illustrating an X-ray fluoroscopy region E1 on a subject and possible positions E2.

FIG. 5 is an explanatory diagram schematically illustrating an X-ray fluoroscopy region E1 on the subject M and possible positions E2 of the specific site C.

In the position selection step (Step S4), a first determination that discriminates one of more possible positions E2 of the specific site C from the X-ray fluoroscopy region E1 on the subject M is made by the discrimination based on the machine learning. Specifically, the entire area of the image of the X-ray fluoroscopy region E1 is sequentially compared with the discriminator, and depending on the degree of similarity to the discriminator, o (correct) or x (incorrect) is determined, and a correct position is discriminated as a possible position of the specific site C. In general, two or three possible positions of the specific site C are discriminated in the one X-ray fluoroscopy region E1. In addition, in the comparison with the discriminator, when a result is outputted not as a binary of o (correct) or x (incorrect) but as a score value, a threshold value for the score value is set, and a position corresponding to a score value equal to or more than the threshold value can be determined as a possible position of the specific site.

Next, the template matching is performed using the multiple templates stored in the image storage step (Step S1) on the one or more possible positions E1 of the specific site C selected in the position selection step, and one position of the specific site C is detected from among the one or more possible positions of the specific site C by making a second determination on the specific site C (Step S5). In the multi-template matching, for example, images of the possible positions E2 of the specific site C in the X-ray fluoroscopy region E1 are compared with the multiple templates stored in the first image storage unit 32 to obtain similarity, and a position of which the degree of similarity is equal to or more than a predetermined threshold value is determined as the position of the specific site C. The position of the specific site is detected at timing corresponding to the fluoroscopy frame rate. As described, it is only necessary to perform the multi-plate matching using the multiple templates not on the entire area of the X-ray fluoroscopy region E1 but on the one or more possible positions E2 selected in the position selection step, and therefore the problem of excessively increasing calculation cost to make real-time processing difficult can be prevented from occurring as conventional.

Then, after the position of the specific site C has been detected, on the basis of the resulting positional information, the radiation beam is radiated from the radiation irradiator 90 to the affected area (specific site C as a tumor) of the subject M. That is, when the position of the affected area is within a predetermined range, the gating of the radiation irradiator 90 is turned ON to radiate the radiation beam to the subject. The detection of the position of the specific site C and the radiation of the radiation beam are repeated until the therapy is ended (Step S6).

As described above, according to the above-described X-ray fluoroscopy device, since the possible positions E2 of the specific site C are determined using the discrimination based on the machine learning, and then from among the possible positions E2, the position of the specific site is detected using the multi-template matching, even when performing the template matching using the multiple templates with use of the images of the specific site C of the subject M instead of a marker, the calculation can be more easily performed to detect the position of the specific site C in real time.

Figure 6:
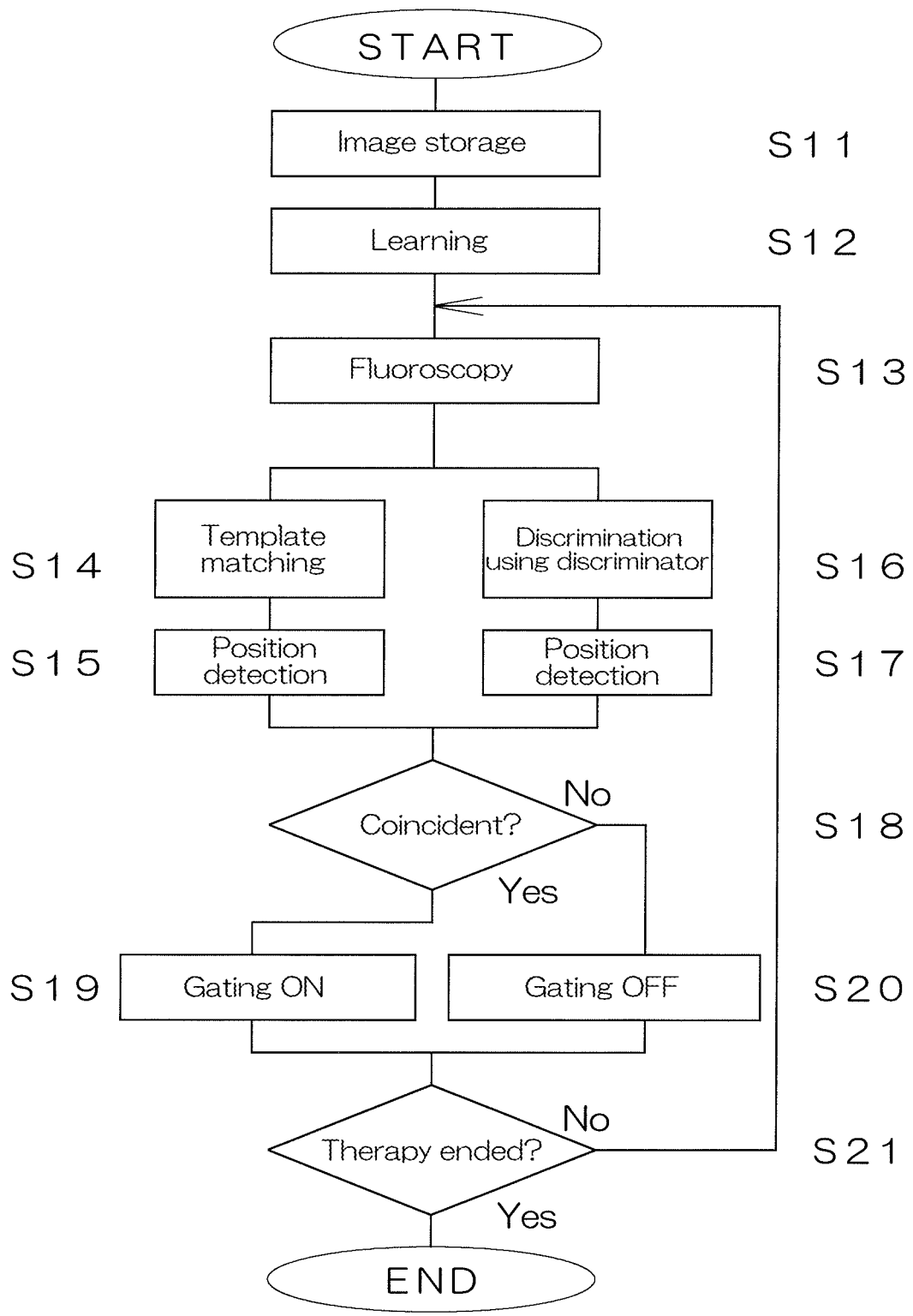
FIG. 6 is a flowchart illustrating a moving body tracking operation using an X-ray fluoroscopy device according to a second embodiment of the present invention.

Next, another embodiment of the present invention will be described. FIG. 6 is a flowchart illustrating a moving body tracking operation using an X-ray fluoroscopy device according to a second embodiment of the present invention.

The above-described embodiment employs a configuration that determines the possible positions E2 of the specific site C using the machine learning and then from among the possible positions E2, detects the position of the specific site C using the multi-template matching. On the other hand, the second embodiment is adapted to more accurately detect the position of a specific site C using both template matching and discrimination based on machine learning.

That is, the template matching is configured to detect as the specific cite C a position of which the degree of similarity is the highest in a search range, and therefore even when the specific site C is arranged outside a range of an image, may detect as the specific site C a position of which the degree of similarity is high. On the other hand, the machine learning is less likely to detect a position other than the specific site C. For this reason, only when as a result of checking the result of the multi-template matching and that of the machine learning with each other, both determine that the same part is the specific site C, it is ultimately determined that the part is the correct position of the specific site C, and thereby detection accuracy can be improved.

When performing moving body tracking using the X-ray fluoroscopy device according to the second embodiment of the present invention, an image storage step is first performed (Step S11). In the image storage step, multiple templates for the template matching are stored in the first image storage unit 32 in the image storage unit 31 illustrated in FIG. 2. Also, multiple positive images for the machine learning are stored in the second image storage unit 33 in the image storage unit 31 illustrated in FIG. 2. Further, in the second image storage unit 33 in the image storage unit 31, negative images used for the machine learning are also stored.

Then, a learning step in the machine learning is performed (Step S12). In the learning step, by performing learning using the multiple positive images stored in the second image storage unit 33, a discriminator for the machine learning is created.

Upon completion of the above preparation steps, X-ray fluoroscopy is performed by the X-ray fluoroscopy device (Step S13) to thereby perform the moving body tracking, as well as radiate a radiation beam from the radiation irradiator 90 to start radiotherapy.

At this time, using the multiple templates stored in the image storage step (Step S11), the template matching is performed (Step S14) to detect the position of the specific site C (Step S15). Also, in parallel to this, discrimination using the discriminator preliminarily created by the machine learning is performed (Step S16) to thereby detect the position of the specific site C (Step S17). Note that a discrimination method using the discriminator is the same as that in the previous embodiment.

Then, it is determined whether or not the position of the specific site C detected by the multi-template matching and the position of the specific site C detected by the discrimination based on the machine learning are coincident with each other (Step S18). When the position of the specific site C detected by the multi-template matching and the position of the specific site C detected by the discrimination based on the machine learning are coincident with each other, the positions are determined to be the position of the specific site C to turn ON a gating (Step S19). On the other hand, when the position of the specific site C detected by the multi-template matching and the position of the specific site C detected by the discrimination based on the machine learning are not coincident with each other, the position of the specific site C is not determined and the gating is turned OFF (Step S20). The detection of the position of the specific site C and the radiation of the radiation beam are repeated until the end of therapy (Step S21).

In addition, in the embodiment illustrated in FIG. 6, the position detection by the template matching (Step S14, Step S15) and that by the machine learning (Step S16, Step S17) are performed in parallel. However, after performing the template matching (Step S14, Step S15), the position detection by the machine learning (Step S16, Step S17) may be performed. Also, as in the above-described first embodiment, after performing the position detection by the machine learning (Step S16, Step S17), the template matching (Step S14, Step S15) may be performed. Further, score values corresponding to the degrees of similarity to the specific site C may be calculated by both of the multi-template matching and the machine learning, and when the sum or product of the score value detected by the multi-template matching and the score value detected by the machine learning is equal to or more than a predetermined threshold value, the position of the specific site C may be specified. In the above embodiment, the multi-template matching using the multiple templates is performed; however, template matching may be performed using one template.

Figure 7:
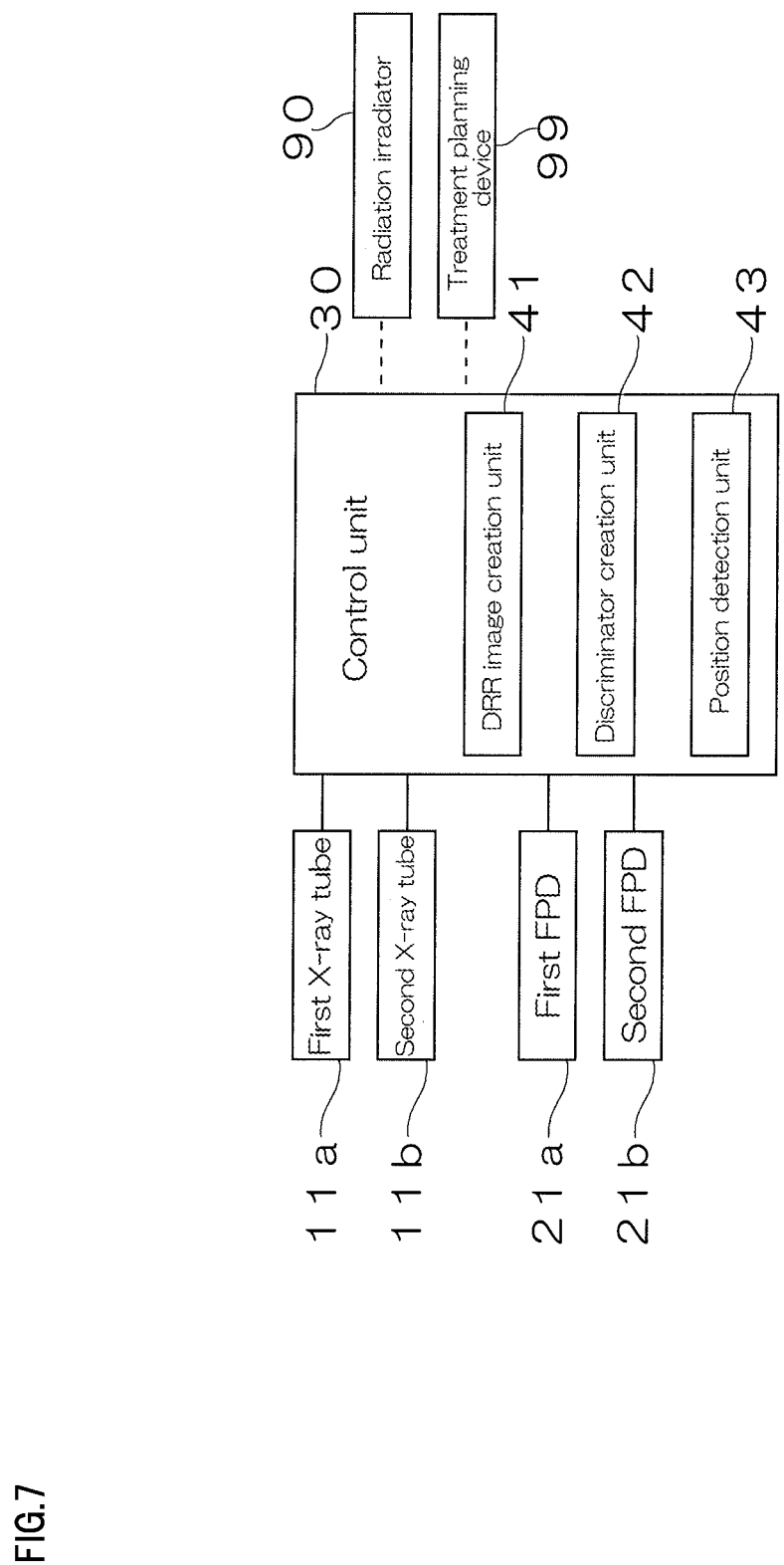
FIG. 7 is a block diagram illustrating a main control system of an X-ray fluoroscopy device according to a third embodiment of the present invention.

Next, still another embodiment of the present invention will be described. FIG. 7 is a block diagram illustrating a main control system of an X-ray fluoroscopy device according to a third embodiment of the present invention.

The X-ray fluoroscopy device is provided with a control unit 30 that includes: a CPU as a processor that performs logic operations; a ROM in which an operation program required to control the device is stored; a RAM in which data and the like are temporarily stored at the time of control; and the like, and controls the whole of the device. The control unit 30 is connected to the above-described first X-ray tube 11a, second X-ray tube 11b, first flat panel detector 21a, and second flat panel detector 21b. In addition, the control unit 30 includes the below-described DRR image creation unit 41, discriminator creation unit 42, and position detection unit 43.

Also, the control unit 30 is connected to the above-described radiation irradiator 90 and to a treatment planning device 99. In addition, the control unit 30 and the treatment planning device 99 may be connected via a radiology information system (RIS) that is in-hospital communication in a subject management system in a hospital. Note that the treatment planning device 99 is one for creating a treatment plan prior to radiotherapy. The treatment planning device stores four-dimensional CT image data consisting of a three-dimensional CT image data group that is obtained by continuously performing three-dimensional CT imaging of a subject by a CT imaging device multiple times and on a region including a specific site at multiple continuous breathing phases of the subject. Then, a treatment plan for the subject is created on the basis of the four-dimensional CT image data and other pieces of data on the subject.

Figure 8:
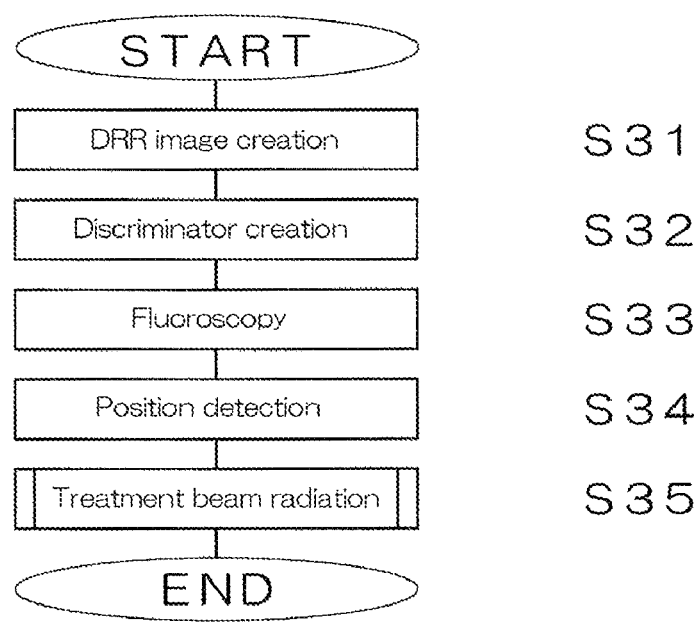
FIG. 8 is a flowchart illustrating a moving body tracking operation using the X-ray fluoroscopy device according to the third embodiment of the present invention.

Next, an operation of using the X-ray fluoroscopy device having the configuration as described above to thereby perform moving body tracking that detects the position of the specific site moving along with the body movement of the subject will be described. FIG. 8 is a flowchart illustrating the moving body tracking operation using the X-ray fluoroscopy device according to the third embodiment of the present invention.

When performing X-ray fluoroscopy, multiple DRR images including the specific site are first created by the DRR image creation unit 41 illustrated in FIG. 7 on the basis of the four-dimensional CT image data created at the time of storing the treatment plan (Step S31). At the time of creating the DRR images, virtual fluoroscopic projection simulating geometric fluoroscopic conditions of the X-ray tubes 11a, 11b and the flat panel detectors 21a, 21b with respect to the subject is performed. Note that the four-dimensional CT data created at the time of creating the treatment plan refers to the three-dimensional CT data group on the region including the specific site continuously imaged with time at the multiple continuous breathing phases.

In the DRR image creating step, on the basis of all pieces of CT image data among the four-dimensional CT data created at the time of creating the treatment plan, or on the basis of pieces of CT image data at multiple breathing phases including breathing phases at which a treatment beam is radiated from the radiation irradiator 90 to at least the subject among the four-dimensional CT data created at the time of creating the treatment plan, the multiple DRR images including the specific site are created.

Then, using the multiple DRR images created by the DRR image creation unit 41, a discriminator for recognizing the specific site using machine learning is created by the discriminator creation unit 42 illustrated in FIG. 7 (Step S32). At this time, a large number of positive images are created by changing parameters for the DRR image creation, such as a projection coordinate and an angle, in the four-dimensional CT image data. In so doing, as necessary, from positions and sizes of the specific site in the four-dimensional CT image data registered in the treatment plan, the positions and sizes of the specific site on the DRR images may be recognized to automatically perform trimming.

At the time of the DRR image creation for creating the positive images, the DRR images are created by changing the parameters for the DRR image creation, which include at least one of the projection coordinate and the angle, on the four-dimensional CT image data. Alternatively, image processing including at least one of slight translation, rotation, deformation, and scaling is performed. The reason to perform translation, rotation, deformation, and scaling is to make it possible to surely track the specific site even when the specific site of the subject, such as a tumor, is non-reproducibly moved or deformed in the body of the subject with respect to the four-dimensional CT image data.

In addition, the frame rate of the four-dimensional CT image data serving as a source of the DRR images is smaller than the frame rate of X-ray fluoroscopic images; however, by changing the parameters for the DRR image creation, the specific site on DRR images between frames can be simulated. Also, an X-ray fluoroscopic image is a transmission image, and therefore a higher contrast background than the specific site, such as a bone region or the diaphragm, is imaged superimposed on the region of the specific site. In contrast to this, changing the parameters as described above causes the superimposition of the background on the specific site to be variously changed, and therefore by learning this, the effect of superimposition of the background can be prevented.

In addition, at least one of contrast change, noise addition, and edge enhancement is performed on the created DRR images. The reason to perform contrast change, noise addition, and edge enhancement is to make it possible to surely track the specific site by accommodating the difference in image quality between the DRR images and X-ray images.

The above-described changes of the parameters for the DRR image creation, such as the projection coordinate and the angle, or the contrast change, noise addition, and edge enhancement are performed randomly within a predetermined range or in a mode that variously makes a change at regular intervals. This makes it possible to create a large number of DRR images from four-dimensional CT image data on one patient. For this reason, using a large number of DRR images created as described, a custom-made discriminator corresponding to each patient can be learned. In addition, a discriminator can also be learned using DRR images on a large number of patients.

Negative images used together with the positive images are created by, for example, the following method. That is, when creating negative images, the negative images are created by, from the DRR images including the specific site created by the DRR image creation unit 41, performing trimming multiple times at random positions avoiding the specific site, i.e., at positions on the background of a specific image. Also, when creating negative images, the negative images are further created using DRR images not including the specific site.

The above-described machine learning work can be preliminarily performed prior to radiotherapy. For this reason, the subject can be prevented from being temporally restrained as in the case of creating templates just before radiotherapy, and also the throughput of radiotherapy can be improved.

As the machine learning used in this discriminator creation step, for example, SVM (Support Vector Machine) can be used. The SVM is one of learning models most superior in quickness and high in recognizing performance among many methods when performing pattern recognition. Also, as the machine learning superior in recognition performance, instead of the SVM, Boosting based on a Haar-like feature value or the like, or a neural network such as Deep Learning may be used.

After the discriminator has been created in the step as described above, X-ray fluoroscopy is performed using the above-described first X-ray imaging system and second X-ray imaging system (Step S33). Then, the position detection unit 43 illustrated in FIG. 7 detects the position of the specific site by performing discrimination using the discriminator created previously (step S34). By continuously performing the X-ray fluoroscopy and the detection of the position of the specific site, the moving body tracking that tracks the position of the specific site is performed.

Then, in this state, the treatment beam is radiated from the radiation irradiator 90 (Step S35). That is, only when the position of the specific site coincides with the specific position, the treatment beam is radiated to perform the radiotherapy.

According to the X-ray fluoroscopy device according to the third embodiment, the machine learning work can be preliminarily performed prior to the radiotherapy, and therefore the radiotherapy can be performed immediately after positioning of the subject.

Also, according to the X-ray fluoroscopy device according to the third embodiment, since the machine learning is performed using not X-ray images but the DRR images, the machine learning itself can be efficiently and quickly performed. That is, in general, in machine learning, practical discrimination accuracy cannot be achieved without 1000 or more learning images. However, in order to acquire X-ray images, X-ray fluoroscopy is required just before therapy to take time, and in addition, when creating positive images, manual trimming by an operator is required, thus making it difficult to prepare a large number of positive images. According to the third embodiment, such problems can be solved by using DRR images.

Further, according to the X-ray fluoroscopy device according to the third embodiment, on the basis of all pieces of CT image data among the four-dimensional CT data created at the time of creating the treatment plan, or on the basis of pieces of CT image data at multiple breathing phases including breathing phases at which the treatment beam is radiated from the radiation irradiator 90 to at least the subject among the four-dimensional CT data created at the time of creating the treatment plan, the multiple DRR images including the specific site are created. For this reason, learning can be performed on the specific site present in the pieces of CT images in common, and also a background not present in common can be prevented from being learned. Accordingly, by performing discrimination on the basis of the result of the learning, the bone region or the like of the subject, which exhibits different movement from the specific site of the subject, can be prevented from being recognized. Also, a background exhibiting the same movement as the specific site of the subject, which present in the pieces of CT image data in common, can be learned, and therefore, for example, even when the contrast of the specific site is extremely small, the background exhibiting the same movement as the specific site can be tracked instead of the specific site. For this reason, by tracking the background, the treatment beam can be radiated to an accurate position to perform the radiotherapy.

Figure 9:
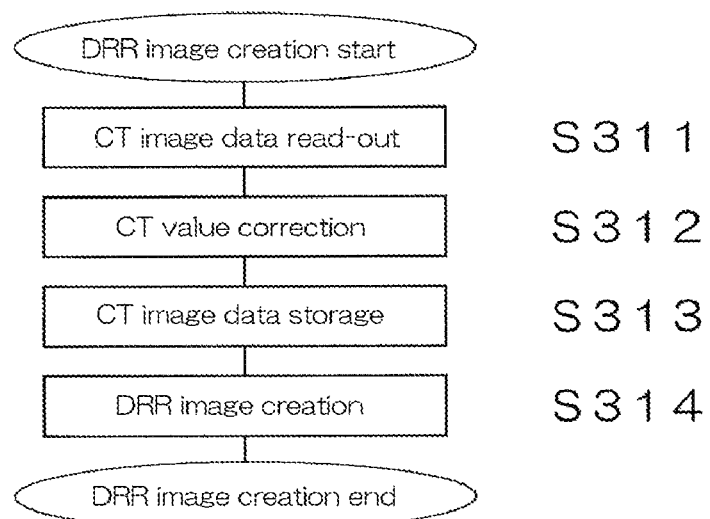
FIG. 9 is a flowchart illustrating a DRR creation process by an X-ray fluoroscopy device according to a fourth embodiment of the present invention.

Next, yet another embodiment of the present invention will be described. FIG. 9 is a flowchart illustrating a DRR creation process by an X-ray fluoroscopy device according to a fourth embodiment of the present invention.

In the fourth embodiment, only the DRR image creation step (Step S31) in the above-described third embodiment is different. That is, in this fourth embodiment, on the basis of CT image data created at the time of storing a treatment plan, the DRR image creation unit 41 creates DRR images in which a specific site of a subject is included and from which a bone region of the subject is removed.

In a DRR image creation step (Step S31) in the fourth embodiment, the CT image data is first read (Step S311). The CT image data may be four-dimensional CT data as in the above-described third embodiment, or may be three-dimensional CT data.

Then, a CT value in the read CT image data is corrected (Step S312). That is, in a CT image, the CT value of a region corresponding to the bone region of the subject is approximately 1000 to 1500, and the CT value of a region corresponding to soft tissue is approximately 0 to 200. For this reason, by recognizing a region whose CT value in the CT image data is 1000 or more as the bone region, and extrapolating the CT value of the soft tissue around it with respect to the CT value of the region, the CT value of the region is converted to the CT value of the soft tissue. In addition, instead of the extrapolation, the CT value of the region may be converted to 200 that is the typical CT value of soft tissue. Then, the CT image data in which the CT value is corrected is stored (Step S313).

After that, the DRR images are created (Step S314). At this time, the CT value of the bone region of the subject is removed from the CT image data, and therefore information on the bone region of the subject is removed from the created DRR images. For this reason, in a discriminator creation step (Step S32) in the subsequent stage, a more accurate discriminator can be created by machine learning focusing on the specific site of the subject.

Figure 10:
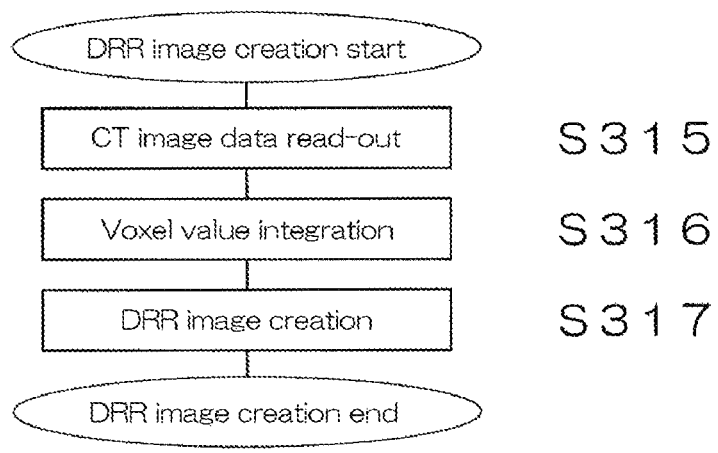
FIG. 10 is a flowchart illustrating a DRR creation process by an X-ray fluoroscopy device according to a fifth embodiment of the present invention.

Next, a still yet another embodiment of the present invention will be described. FIG. 10 is a flowchart illustrating a DRR creation process by an X-ray fluoroscopy device according to a fifth embodiment of the present invention.

In the fifth embodiment, as in the above-described fourth embodiment, only the DRR image creation step (Step 31) in the third embodiment is different. That is, in the fifth embodiment as well, on the basis of CT image data created at the time of storing a treatment plan, the DRR image creation unit 41 creates DRR images in which a specific site of a subject is included and from which a bone region of the subject is removed.

In a DRR image creation step (Step S31) in the fifth embodiment, the CT image data is first read (Step S315). The CT image data may be four-dimensional CT data as in the above-described third embodiment, or may be three-dimensional CT data.

Then, virtual projection is performed on the read CT data, and the line integral of a voxel value in the CT image data is performed (Step S316). At the time of the line integral of a voxel value, by recognizing a region whose CT value in the CT image data is 1000 or more as a bone region, and extrapolating the CT value of soft tissue around it with respect to the CT value of the region, the CT value of the region is converted to the CT value of the soft tissue to perform the line integral. In addition, instead of the extrapolation, the CT value of the region may be converted to 200, which is a typical CT value of soft tissue, to perform the line integral.

Then, from the result of the line integral, the DRR images are created (Step S317). At this time, as in the case of the above-described fourth embodiment, information on the bone region of the subject is removed from the created DRR images. For this reason, in a discriminator creation step (Step S32) in the subsequent stage, a more accurate discriminator can be created by machine learning focusing on the specific site of the subject.

Figure 11:
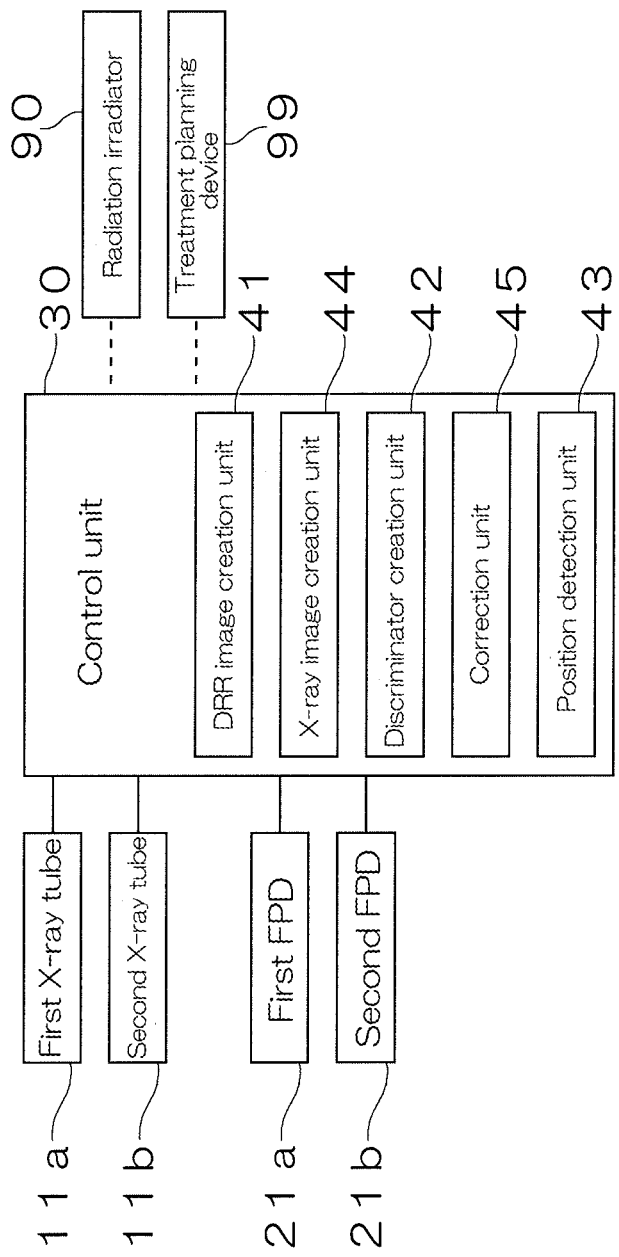
FIG. 11 is a block diagram illustrating a main control system of an X-ray fluoroscopy device according to a sixth embodiment of the present invention.
Figure 12:
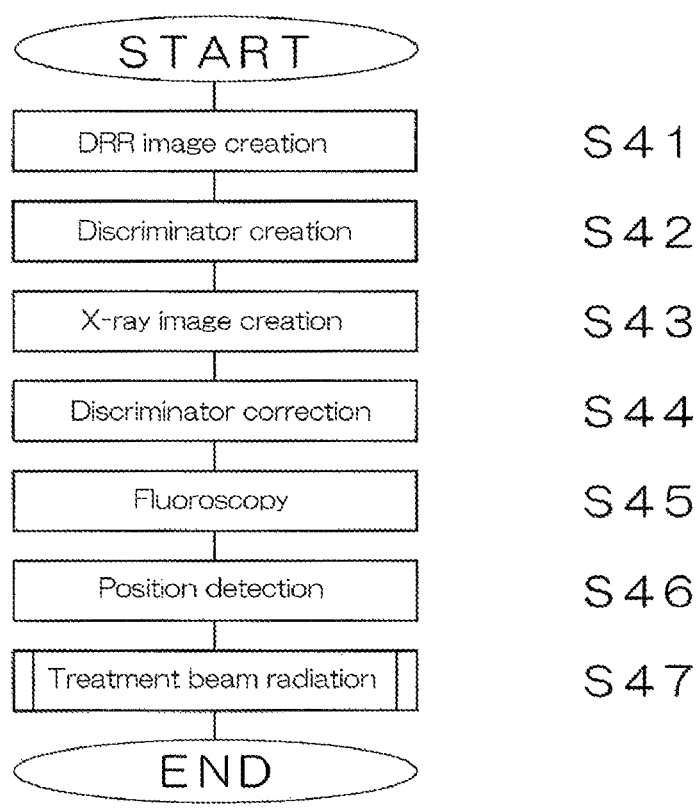
FIG. 12 is a flowchart illustrating a moving body tracking operation using the X-ray fluoroscopy device according to the sixth embodiment of the present invention.

Next, further another embodiment of the present invention will be described. FIG. 11 is a block diagram illustrating a main control system of an X-ray fluoroscopy device according to a sixth embodiment of the present invention. Also, FIG. 12 is a flowchart illustrating a moving body tracking operation using the X-ray fluoroscopy device according to the sixth embodiment of the present invention. In addition, the same members as in the above-described third embodiment are marked with the same symbols to omit detailed description.

As illustrated in FIG. 11, a control unit 30 in the X-ray fluoroscopy device according to the sixth embodiment includes: the DRR image creation unit 41, an X-ray image creation unit 44, the discriminator creation unit 42, a correction unit 45, and the position detection unit 43. In addition, the X-ray fluoroscopy device according to the sixth embodiment employs a configuration in which the correction unit 45 corrects a discriminator created in the discriminator creation unit 42 using X-ray images created by the X-ray image creation unit 44.

In the X-ray fluoroscopy device according to the sixth embodiment, as in the case of the above-described third embodiment, DRR images are created by the DRR image creation unit 41 (Step S41), and then the discriminator is created using machine learning by the discriminator creation unit 42 (Step S42). This work is preliminarily performed prior to radiotherapy as in the above-described third embodiment.

Then, the X-ray image creation unit 44 illustrated in FIG. 11 creates the multiple X-ray images including a specific site by collecting images including the specific site of a subject (Step S43). At this time, the above-described first X-ray imaging system and second X-ray imaging system are used. From the X-ray images imaged by the X-ray imaging systems, only regions of the specific site are trimmed as necessary.

Then, in the same manner as in the case of the DRR images, from the X-ray images of the specific site, positive images used for the machine learning are created. Also, as in the case of the DRR images, by performing trimming multiple times at random positions avoiding the specific site on the X-ray images including the specific site, that is, at positions on the background of a specific image, and using images not including the specific site, negative images are created.

After that, the previously created discriminator is corrected by the correction unit 45 (Step S44). This makes it possible to create a discriminator having higher accuracy. At this time, when SVM is used as the machine learning, a new discriminator is created by performing the machine learning using the X-ray images, and the new discriminator is added used in combination with the previously created discriminator. Alternatively, separating hyperplane parameters of the previously created discriminator and new discriminator are synthesized to correct the discriminator itself. Also, when Boosting is used as the machine learning, the machine learning is performed using the X-ray image to create a new weak discriminator, and the new weak discriminator is added to the previously created discriminator that is a group of weak discriminators. Further, when a neural network such as Deep Learning is used as the machine learning, the discriminator itself is corrected by further performing the machine learning using the X-ray images with a parameter of the previously created discriminator as an initial value. The correction of the discriminator in this specification is a concept including both of the addition of a new discriminator to the above-described discriminator and the correction of the discriminator itself.

After the discriminator has been corrected in the step as described above, X-ray fluoroscopy is performed (Step S45).

Then, the position detection unit 43 illustrated in FIG. 11 detects the position of the specific site by performing discrimination (Step S46). By continuously performing the X-ray fluoroscopy and the detection of the position of the specific site, moving body tracking that tracks the position of the specific site is performed. Then, in this state, a treatment beam is radiated by the radiation irradiator 90 (Step S47).

According to the X-ray fluoroscopy device according to the sixth embodiment, since the discriminator created in the discriminator creation unit 42 is corrected using the X-ray images, the position of the specific site can be more accurately detected. At this time, the machine learning based on the DRR image is preliminarily performed, and therefore the discriminator can be corrected without using a large number of X-ray images. For this reason, complicated manual trimming work or the like by an operator as described above can be reduced, and the effort and time for correcting the discriminator can be reduced.

Figure 13:
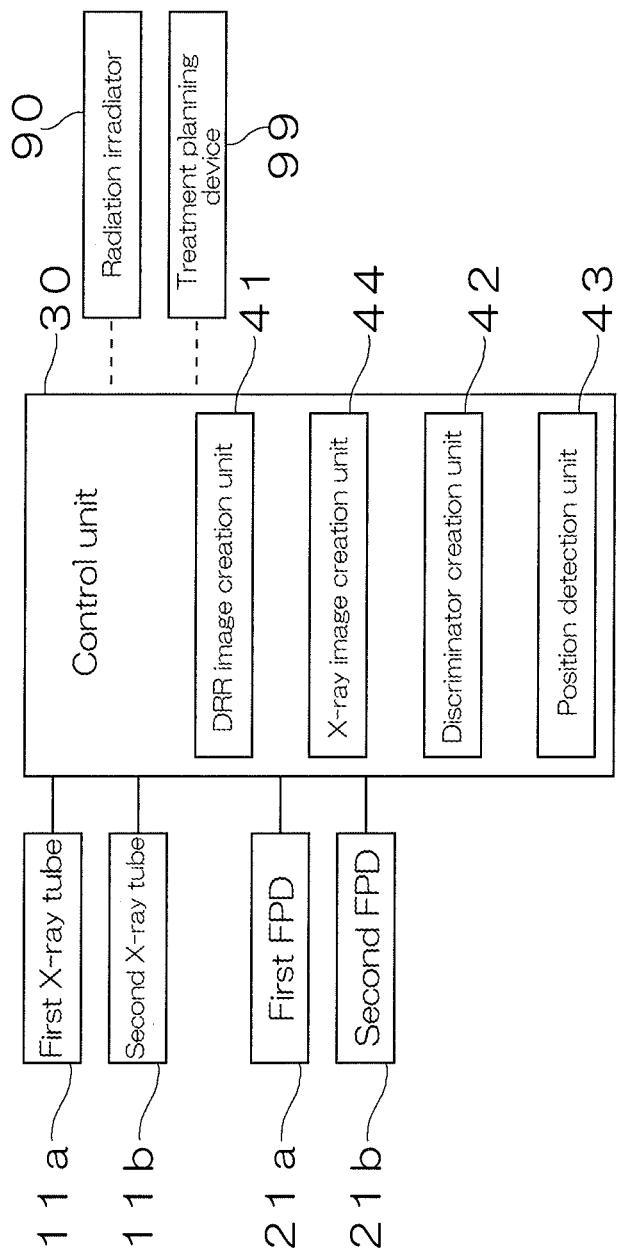
FIG. 13 is a block diagram illustrating a main control system of an X-ray fluoroscopy device according to a seventh embodiment of the present invention.
Figure 14:
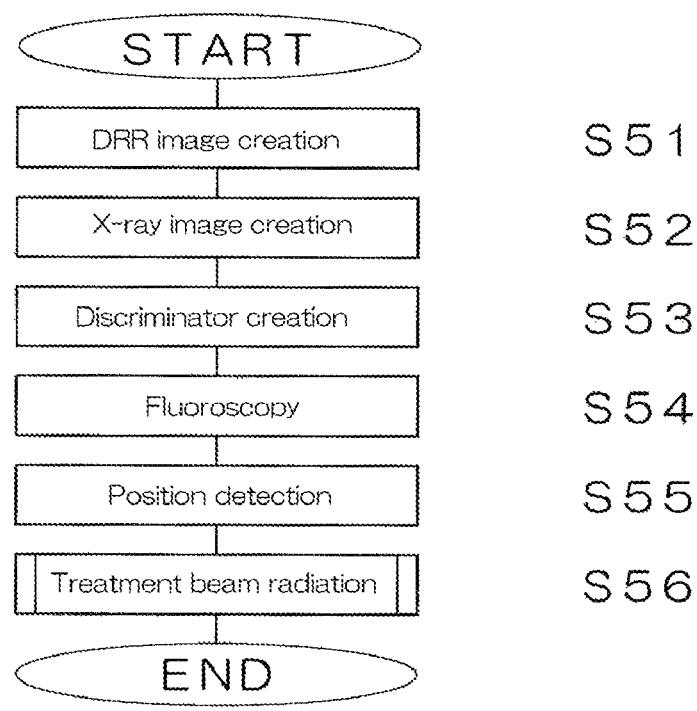
FIG. 14 is a flowchart illustrating a moving body tracking operation using the X-ray fluoroscopy device according to the seventh embodiment of the present invention.

Next, still further another embodiment of the present invention will be described. FIG. 13 is a block diagram illustrating a main control system of an X-ray fluoroscopy device according to a seventh embodiment of the present invention. Also, FIG. 14 is a flowchart illustrating a moving body tracking operation using the X-ray fluoroscopy device according to the seventh embodiment of the present invention. In addition, the same members as in the above-described third embodiment and sixth embodiment are marked with the same symbols to omit detailed description.

As illustrated in FIG. 13, a control unit 30 in the X-ray fluoroscopy device according to the seventh embodiment includes the DRR image creation unit 41, the X-ray image creation unit 44, the discriminator creation unit 42, and the position detection unit 43. In addition, the X-ray fluoroscopy device according to the seventh embodiment employs a configuration in which the discriminator creation unit 42 creates a discrimination for recognizing a specific site by performing machine learning on DRR images created in the DRR image creation unit 41 and X-ray images created in the X-ray image creation unit 44.

In the X-ray fluoroscopy device according to the seventh embodiment, as in the cases of the above-described third embodiment and sixth embodiment, the DRR images are created by the DRR image creation unit 41 (Step S51). Also, the X-ray image creation unit 44 illustrated in FIG. 13 creates the multiple X-ray images including the specific site by collecting images including the specific site of a subject (Step S52).

Then, the discriminator is created using the machine learning by the discriminator creation unit 42 illustrated in FIG. 13 (Step S53). At this time, as in the cases of the first and sixth embodiments, the discriminator is created by simultaneously performing the machine learning of the DRR images and the machine learning of the X-ray images using positive images and negative images created on the basis of the DRR images, as well as using positive images and negative images created on the basis of the X-ray images.

As described, in the seventh embodiment, the discriminator for recognizing the specific site is created by performing the machine learning on the DRR images created in the DRR image creation unit 41 and on the X-ray images created in the X-ray image creation unit 44. For this reason, the accuracy of the discriminator can be made high. Also, as described above, a large number of learning images are required for machine learning; however, in order to acquire X-ray images for machine learning using the X-ray images, there occurs the problem of not only requiring X-ray fluoroscopy just before therapy to take time but when creating positive images, requiring manual trimming by an operator to make it difficult to prepare a large number of positive images. According to the seventh embodiment, the number of required X-ray images can be made small by using the DRR images, and the discriminator can be more efficiently created.

In addition, in the above description, the X-ray images are created after creating the DRR images, but this order may be reversed. Alternatively, the creation of the DRR images and the creation of the X-ray images may be simultaneously performed.

After the discriminator has been created in the step as described above, the X-ray fluoroscopy is performed (Step S54). Then, the position detection unit 43 illustrated in FIG. 13 detects the position of the specific site by performing discrimination (Step S55). By continuously performing the X-ray fluoroscopy and the detection of the position of the specific site, moving body tracking that tracks the position of the specific site is performed. Then, in this state, a treatment beam is radiated by the radiation irradiator 90 (Step S56).

According to the X-ray fluoroscopy device according to the seventh embodiment, by performing the machine learning on the DRR images created on the basis of the four-dimensional CT image data and on the X-ray images created by the X-ray imaging, the position of the specific site can be more accurately detected. At this time, since the machine learning based on the DRR images and the machine learning based on the X-ray images are used in combination, the discriminator can be quickly created without using a large number of X-ray images.

Figure 15:
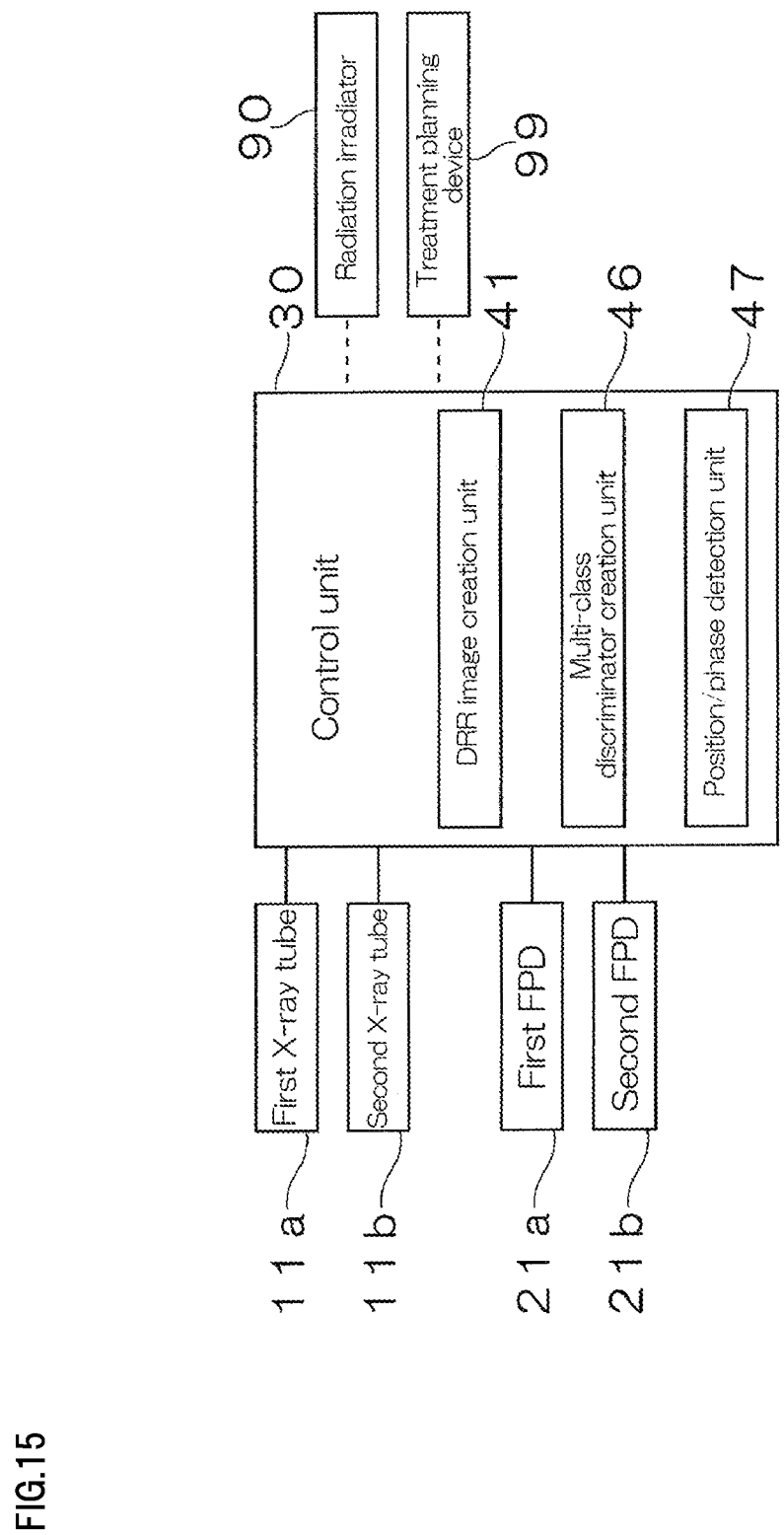
FIG. 15 is a block diagram illustrating a main control system of an X-ray fluoroscopy device according to an eighth embodiment of the present invention.

Next, yet further another embodiment of the present invention will be described. FIG. 15 is a block diagram illustrating a main control system of an X-ray fluoroscopy device according to an eighth embodiment of the present invention. In addition, the same components as in the above-described third embodiment are marked with the same symbols to omit detailed description.

In the above-described third embodiment to seventh embodiment, as a discriminator for recognizing a specific site using machine learning, a two-class discriminator is used, whereas in the eighth embodiment, a multi-class discriminator for discriminating a specific site at each breathing phase is used. That is, in the eighth embodiment, as the discriminator creation unit 42 in the above-described third embodiment, in particular, a multi-class discriminator creation unit 46 is employed, and the multi-class discriminator creation unit 46 creates the multi-class discriminator for discriminating the specific site at each breathing phase. Also, in the eighth embodiment, as the position detection unit 43 in the above-described third embodiment, a position/phase detection unit 47 is employed to employ a configuration in which the position and phase of the specific site are detected.

Figure 16:
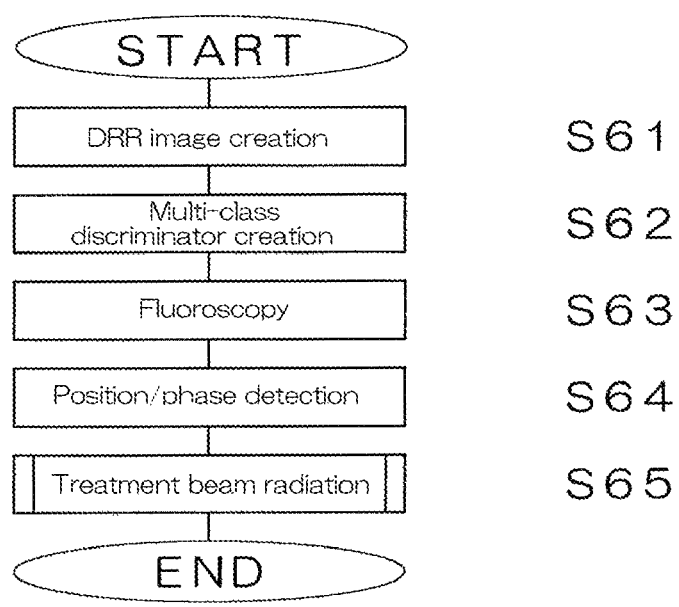
FIG. 16 is a flowchart illustrating a moving body tracking operation using the X-ray fluoroscopy device according to the eighth embodiment of the present invention.

FIG. 16 is a flowchart illustrating a moving body tracking operation using the X-ray fluoroscopy device according to the eighth embodiment of the present invention.

When performing X-ray fluoroscopy, as in the case of the above-described third embodiment, multiple DRR images including the specific site are first created by the DRR image creation unit 41 illustrated in FIG. 15 on the basis of four-dimensional CT image data created at the time of storing a treatment plan (Step S61). In this DRR image creation step, the multiple DRR images including the specific site are created on the basis of all pieces of CT image data among the four-dimensional CT data created at the treatment planning time, or on the basis of pieces of CT image data at multiple breathing phases including breathing phases at which a treatment beam is radiated from the radiation irradiator 90 to at least a subject among the four-dimensional CT data created at the treatment planning time.

Then, using the multiple DRR images created by the DRR image creation unit 41, the multi-class discriminator for recognizing the position of the specific site and a breathing phase is created using machine learning by the multi-class discriminator creation unit 46 illustrated in FIG. 15 (Step S62). At this time, a large number of positive images are created at each breathing phase by changing parameters for the DRR image creation, such as a projection coordinate and an angle, in the four-dimensional CT image data.

At this time, the multi-class discriminator is created by the machine learning using large numbers of positive images and negative images created in the same manner as in the case of the above-described third embodiment. The machine learning work can be preliminarily performed prior to radiotherapy. For this reason, the subject can be prevented from being temporally restrained as in the case of creating templates just before radiotherapy, and the throughput of radiotherapy can be improved.

As the machine learning used in this multi-class discriminator creation step, for example, Deep Learning typified by a convolutional neural network (CNN) can be used. The convolutional neural network is one of learning models highest in recognizing performance among many methods when performing pattern recognition.

Figure 17:
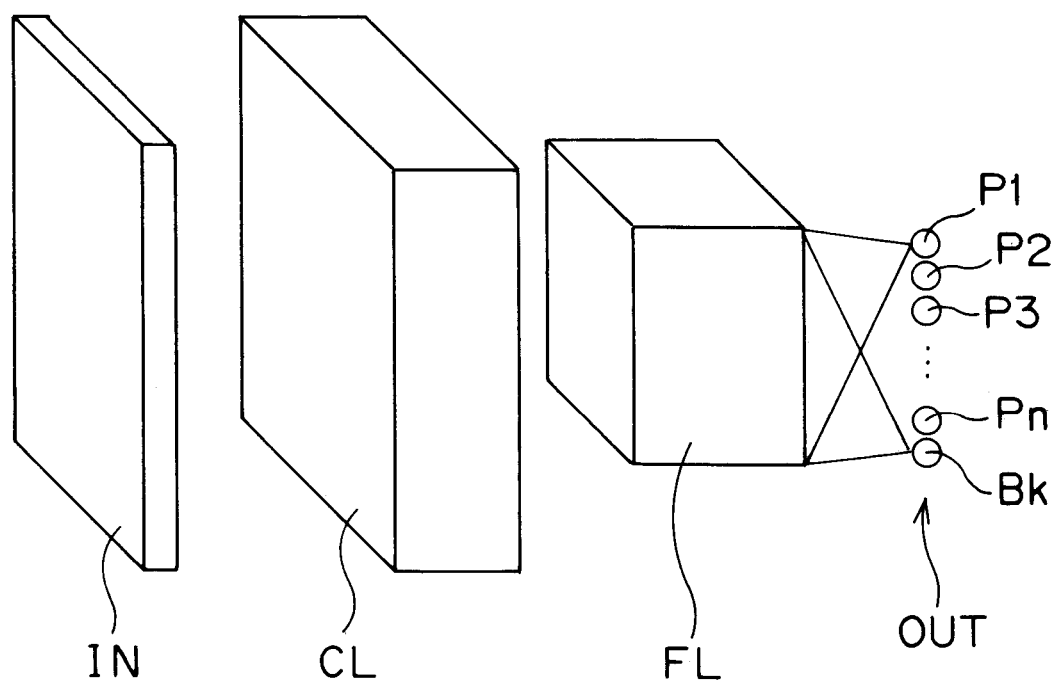
FIG. 17 is an explanatory diagram for explaining the concept of a convolutional neural network.

FIG. 17 is an explanatory diagram for explaining the concept of the convolutional neural network.

The convolutional neural network has a configuration in which between an input layer IN consisting of X-ray fluoroscopic images and an output layer OUT consisting of multiple nodes, a convolution layer CL and a fully connected layer FL as intermediate layers are arranged. The convolutional neural network has a configuration in which the fully connected layer FL corresponding to a neural network is added with the convolution layer CL in which a convolution process is performed.

As illustrated in FIG. 17, the output layer OUT consists of n nodes P1 to Pn corresponding to breathing phases of the subject and a node Bk corresponding to a background, and is normalized by a softmax function such that the total value of the values of all the nodes is 1. That is, each node has a value corresponding to a probability at which an input image belongs to each class. In the convolution layer CL and the fully connected layer FL, parameters are determined by learning. At the time of the learning, when inputting a positive image at a breathing phase m (m is an integer equal to or more than 1 and equal to or less than n), the value of a node Pmn corresponding to the breathing phase m is set to 1 as a correct output value, and the value of the other nodes are set to 0. Also, when inputting a negative image, the value of the background node Bk is set to 1, and the values of the other nodes are set to 0. This allows the machine learning to be performed.

After the discriminator has been created in the step as described above, the X-ray fluoroscopy is performed using the above-described first X-ray imaging system and second X-ray imaging system (Step S63). Then, the position/phase detection unit 47 illustrated in FIG. 15 detects the position of the specific site and a breathing phase of the subject at the time by performing discrimination using the previously created discriminator (Step S64).

At the time of detecting the specific site, an image of a detection window for searching X-ray fluoroscopic images is inputted, and a node whose output value (probability) is the largest at the time is detected. That is, when the value of the background node is the maximum, it is determined that the specific site is not detected, and when the value of a node Pn corresponding to a breathing phase n is the maximum, it is determined that the specific site is detected, and a breathing phase at the time is n.

By continuously performing the above-described X-ray fluoroscopy, and the detection of the position of the specific site and a breathing phase of the subject, moving body tracking that tracks the position of the specific site and a breathing phase of the subject at the time is performed. Then, in this state, the treatment beam is radiated by the radiation irradiator 90 (Step S65). That is, only when the position of the specific site coincides with a specific position, and a breathing phase of the subject at the time coincides with a breathing phase planned at the treatment planning time, the treatment beam is radiated to perform the radiotherapy.

In addition, since a breathing phase of the subject continuously changes, the breathing phase is strictly a breathing phase between nodes whose output values are the largest and the second largest. Accordingly, weighting based on the node values of both may be performed to interpolate between breathing phases. By preliminarily interpolating between breathing phases to obtain positions of the specific site on the DRR images by interpolating between breathing phases, the position of the specific site predicted from a breathing phase obtained by the interpolation can be acquired.

Figure 18:
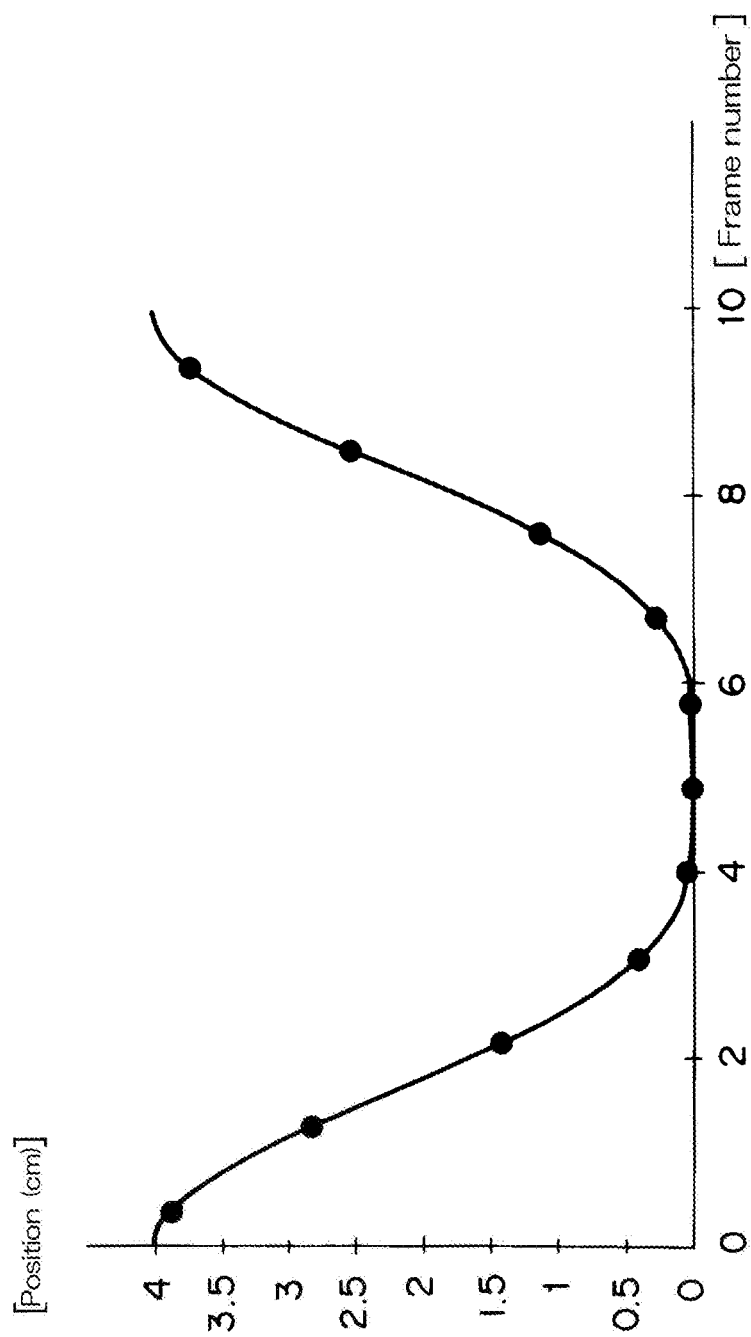
FIG. 18 is a graph illustrating a periodic function usable for interpolation.

FIG. 18 is a graph illustrating a periodic function usable for such interpolation. In addition, this graph is one assuming a case in which during one cycle of breathing of the subject, DRR images of 10 frames are created at regular time intervals. In this graph, the vertical axis represents the Y-directional position (cm) of the specific site on a DRR image with the position of the specific site when a breathing phase of the subject reaches the maximum breathing phase being as a reference, and the horizontal axis represents a breathing phase (the frame number of a DRR image created on the basis of the four-dimensional CT image data). Note that the Y-direction refers to the main moving direction of the specific site. The specific site moves in the X, Y directions on a DRR image, and FIG. 18 illustrates a Y-directional position on each DRR image. The same holds true for an X-directional position.

The position of the specific site associated with a breathing phase of the subject can be highly accurately interpolated by performing the regression of the periodic function simulating a breathing phase of the subject as illustrated in FIG. 18.

In addition, this can also be used to prevent the treatment beam from being erroneously radiated, such as comparing the position of the specific site predicted from a breathing phase and the detected position of the specific site, and as erroneous detection, determining a case in which there is a large deviation between them. Also, both positions of the specific site may be synthesized to calculate the ultimate position of the specific site.

Further, machine learning may performed on a first discriminator with the specific site and the background as two class classification as in the above-described third embodiment, and when the specific site is detected, a breathing phase may be detected using multi-class classification based on a convolutional neural network as second discrimination.

In general, since the convolutional neural network requires high calculation cost, the specific site is searched for by machine learning requiring small calculation cost, and by performing the convolutional neural network only on the specific site detected by this or only on the periphery of it, the position of the specific site and a breathing phase can be detected at high speed. Alternatively, by repeating the two-class classification multiple times, performing the multi-class classification may be configured.

Figure 19:
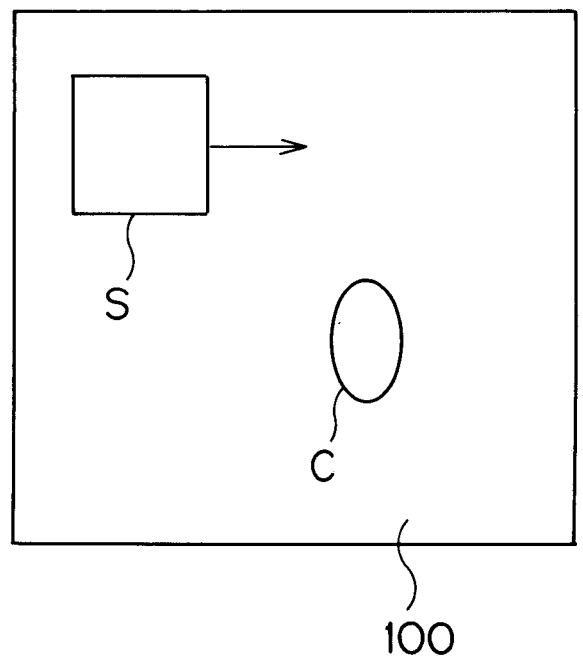
FIG. 19 is a schematic diagram illustrating an operation of finding the position of a specific site using the convolutional neural network.
Figure 20:
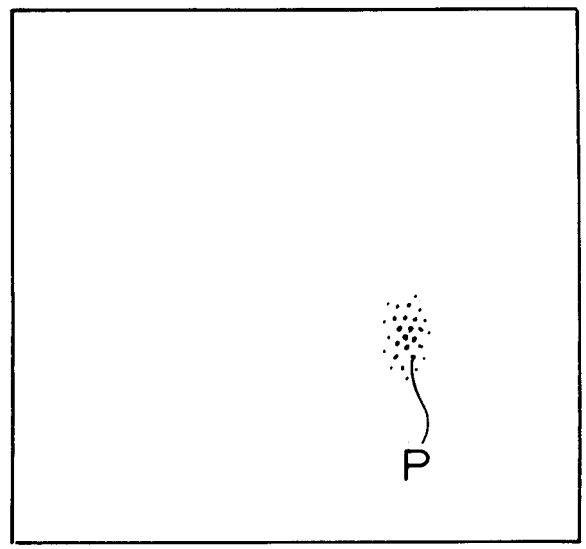
FIG. 20 is a schematic diagram illustrating the operation of finding the position of the specific site using the convolutional neural network.

FIG. 19 and FIG. 20 are schematic diagrams illustrating an operation of finding the position of the specific site using the convolutional neural network. In addition, in FIG. 19, the symbol S represents a search window and the symbol C represents a region of the specific site on an X-ray fluoroscopic image.

As illustrated in FIG. 19, by scanning the search window on the X-ray fluoroscopic image 100, the specific site is searched for. Then, as illustrated in FIG. 20, the probability of the specific site, i.e., a map P of the sum of the values of nodes corresponding to all breathing phases is created. This map P corresponds to a probability distribution (probability density function) of the specific site because the probability is increased around a pixel where the specific site is present. A position at which the probability density function takes the maximum value is a position at which the specific site is detected. The position at which the probability density function takes the maximum value can be highly accurately calculated using sub-pixels by kernel density estimation such as a mean-shift method. Alternatively, the gravity center position of the map P with a probability as weight may be determined as the position at which the specific site C is detected.

According to the X-ray fluoroscopy device according to the eighth embodiment, the position of the specific site and also a breathing phase of the subject at the time can be specified, and therefore when the specific site is at a predetermined position, and a breathing phase of the subject coincides with a specific phase, the treatment beam can be radiated. Accordingly, the radiation beam can be radiated in accordance with the treatment plan.

REFERENCE SIGNS LIST

11a First X-ray tube
11b Second X-ray tube
21a First flat panel detector
21b Second flat panel detector
29 Examination table
30 Control unit
31 Image storage unit
32 First image storage unit
33 Second image storage unit
34 Learning unit
35 Position selection unit
36 Position detection unit
41 DRR image creation unit
42 Discriminator creation unit
43 Position detection unit
44 X-ray image creation unit
45 Correction unit
46 Multi-class discriminator creation unit
47 Position/phase detection unit
90 Radiation irradiator
99 Treatment planning device
E1 X-ray fluoroscopy region
E2 Candidate position
C Specific site
M Subject

The invention claimed is:

1. An X-ray fluoroscopy method that, by making an X-ray detector detect an X-ray radiated from an X-ray tube and passing through a subject and collecting a first image including a specific site of the subject, detects a position of the specific site to track movement of the specific site, the X-ray fluoroscopy method comprising:
  a storage step of storing a template configured for template matching, the template being created on a basis of the first image including the specific site of the subject, and a positive image for machine learning, the positive image being created on a basis of the first image including the specific site of the subject;
  a learning step of, on a basis of the positive image stored in the storage step, creating a discriminator by the machine learning;
  a fluoroscopy step of making the X-ray detector detect the X-ray radiated from the X-ray tube and passing through the subject, and collecting a second image including the specific site of the subject; and
  a position detection step of detecting a position of the specific site by, on the second image obtained in the fluoroscopy step, performing both of the template matching using the template and performing discrimination using the discriminator created by the machine learning.

2. The X-ray fluoroscopy method of claim 1, wherein the machine learning comprises a learning model chosen from the group consisting of a Support Vector Machine (SVM) model, a Boosting model, and a neural network model.

3. The X-ray fluoroscopy method according to claim 1, wherein performing the template matching step is performed before the discrimination step, or alternatively, the discrimination step is performed before the template matching step.

4. The X-ray fluoroscopy method according to claim 1, wherein performing the template matching step is performed simultaneously with the discrimination step.

5. An X-ray fluoroscopy method that, by making an X-ray detector detect an X-ray radiated from an X-ray tube and passing through a subject and collecting a first image including a specific site of the subject, detects a position of the specific site to track movement of the specific site, the X-ray fluoroscopy method comprising:
  a storage step of storing a template configured for template matching, the template being created on a basis of the first image including the specific site of the subject, and a positive image for machine learning;
  a learning step of, on a basis of multiple positive images stored in the image storage step, creating a discriminator by the machine learning;
  a fluoroscopy step of making the X-ray detector detect the X-ray radiated from the X-ray tube and passing through the subject, and collecting a second image including the specific site of the subject;
  a position selection step of, with use of the second image obtained in the fluoroscopy step, selecting a possible position of the specific site by discrimination using the discriminator created by the machine learning; and
  a position detection step of detecting a position of the specific site by performing the template matching using the template stored in the image storage step on the possible position of the specific site, the possible position being selected in the position selection step.

6. The X-ray fluoroscopy method of claim 5, wherein the machine learning comprises a learning model chosen from the group consisting of a Support Vector Machine (SVM) model, a Boosting model, and a neural network model.

7. The X-ray fluoroscopy method of claim 5, wherein the template and the positive image are respectively created based on a same image, and
wherein the same image includes the specific site.

8. An X-ray fluoroscopy method that makes an X-ray detector detect an X-ray radiated from an X-ray tube and passing through a subject to acquire a first image including a specific site of the subject, detects a position of the specific site to track movement of the specific site, the X-ray fluoroscopy method comprising:
a DRR image creation step of creating multiple DRR images including the specific site on a basis of CT image data created at a time of storing a treatment plan;
a discriminator creation step of, by performing machine learning on the DRR images created in the DRR image creation step, creating a discriminator for recognizing the specific site;
a fluoroscopy step of making the X-ray detector detect the X-ray radiated from the X-ray tube and passing through the subject to obtain a second image including the specific site of the subject; and
a position detection step of detecting a position of the specific site by performing discrimination using the discriminator created in the discriminator creation step on the second image obtained in the fluoroscopy step.

9. The X-ray fluoroscopy method according to claim 8, wherein when creating the DRR images further includes performing a line integral of a voxel value in the CT image data created at the time of storing the treatment plan, and, on a basis of the voxel value, the DRR image creation step creates the DRR image in which the specific site is included and from which a bone region of the subject is removed.

10. The X-ray fluoroscopy method according to claim 8, wherein the DRR image creation step further includes:
creating the DRR images by changing parameters, wherein the parameters include at least one of: a projection coordinate and an angle in the geometric fluoroscopic conditions and performing image processing, wherein the image processing includes at least one of: rotation, deformation, and scaling of an image;
performing at least one of: contrast change, noise addition, and edge enhancement on the created DRR images, wherein the DRR images are created, including the specific site, on a basis of four-dimensional CT image data consisting of a three-dimensional CT image data group that is created at the time of storing the treatment plan, and, on a region including the specific site, at multiple continuous breathing phases; and
creating a DRR image, on the basis of the CT image data created at the time of storing the treatment plan, in which the specific site is included and from which a bone region of the subject is removed,
wherein the discriminator creation step further includes recognizing the specific site at each breathing phase of the subject;
a creating multiple X-ray images step of including the specific site by causing the X-ray detector to detect the X-ray radiated from the X-ray tube and passing through the subject;
a collecting an image step including the specific site of the subject;
a correction step that corrects the discriminator;
performing machine learning on the created DRR images and on the created X-ray images; and
recognizing the specific site at each breathing phase of the subject,
wherein the position detection step further includes detecting the position of the specific site and a breathing phase of the subject by performing multi-class discrimination on an image, including the specific site of the subject, the image being obtained by making the X-ray detector detect the X-ray radiated from the X-ray tube that passes through the subject.

11. The X-ray fluoroscopy method according to claim 10, wherein the DRR image creation step further includes creating the multiple DRR images, including the specific site, on a basis of pieces of CT image data at multiple breathing phases that include a breathing phase at which a treatment beam is radiated to the subject among the four-dimensional image data consisting of the three-dimensional CT image data group that is created at the time of storing the treatment plan and on the region including the specific site at the multiple continuous breathing phases.

12. The X-ray fluoroscopy method according to claim 10, wherein creating the DRR images further includes performing a line integral of a voxel value in the CT image data created at the time of storing the treatment plan, and, on a basis of the voxel value, creating the DRR images, in which the specific site is included and from which the bone region of the subject is removed.

* * * * *